(12) United States Patent
Mitan et al.

(10) Patent No.: US 10,342,757 B2
(45) Date of Patent: Jul. 9, 2019

(54) CYTOMIMETIC FORMULATIONS AND METHODS OF MANUFACTURING THE SAME

(71) Applicant: MITANI GROUP, INC., New York, NY (US)

(72) Inventors: Mirela Mitan, East Quogue, NY (US); Mario De Rosa, Naples (IT); Mosè Rossi, Naples (IT)

(73) Assignee: Mitani Group, Inc., New York, NY (US)

( * ) Notice: Subject to any disclaimer, the term of this patent is extended or adjusted under 35 U.S.C. 154(b) by 71 days.

(21) Appl. No.: 15/831,596

(22) Filed: Dec. 5, 2017

(65) Prior Publication Data
US 2018/0169001 A1    Jun. 21, 2018

Related U.S. Application Data

(60) Provisional application No. 62/436,698, filed on Dec. 20, 2016.

(51) Int. Cl.
| | |
|---|---|
| *A61K 36/00* | (2006.01) |
| *A61K 8/9789* | (2017.01) |
| *A61K 8/9728* | (2017.01) |
| *A61K 8/73* | (2006.01) |
| *A61Q 19/08* | (2006.01) |
| *A61K 8/34* | (2006.01) |
| *A61K 8/81* | (2006.01) |
| *A61K 8/893* | (2006.01) |
| *A61K 8/63* | (2006.01) |
| *A61K 8/55* | (2006.01) |
| *A61K 8/25* | (2006.01) |

(52) U.S. Cl.
CPC .............. *A61K 8/9789* (2017.08); *A61K 8/25* (2013.01); *A61K 8/345* (2013.01); *A61K 8/553* (2013.01); *A61K 8/63* (2013.01); *A61K 8/73* (2013.01); *A61K 8/735* (2013.01); *A61K 8/8111* (2013.01); *A61K 8/8147* (2013.01); *A61K 8/8152* (2013.01); *A61K 8/893* (2013.01); *A61K 8/9728* (2017.08); *A61Q 19/08* (2013.01); *A61K 2800/85* (2013.01)

(58) Field of Classification Search
CPC ...................................................... A61K 36/00
USPC ......................................................... 424/725
See application file for complete search history.

(56) References Cited

U.S. PATENT DOCUMENTS

2013/0295140 A1* 11/2013 Shifrine ............... A61K 36/062
424/275.1

\* cited by examiner

*Primary Examiner* — Michael V Meller
(74) *Attorney, Agent, or Firm* — Amster, Rothstein & Ebenstein LLP

(57) ABSTRACT

A cytomimetic formulation is provided comprising at least two of: (a) a fermented truffle extract; (b) a plurality of hyaluronic acids of different molecular weight, ranging from 50 KDa up to 2000 KDa; (c) an olive leaf extract in a mineral-containing water; and (d) a fermented grape must. The formulations mimic the skin cytoplasmic environment and create optimal conditions for cellular growth and skin rejuvenation. Methods of use and processes for manufacturing thereof are also provided.

1 Claim, 3 Drawing Sheets
Specification includes a Sequence Listing.

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: primers directed to human genes

<400> SEQUENCE: 1
tgcggcagct gtacattga                                             19

<210> SEQ ID NO 2
<211> LENGTH: 18
<212> TYPE: DNA
<213> ORGANISM: Artificial Sequence
<220> FEATURE:
<223> OTHER INFORMATION: primers directed to human genes

<400> SEQUENCE: 2
cgagtgacaa gcctgtag                                              18

<210> SEQ ID NO 3
<211> LENGTH: 20
<212> TYPE: DNA
<213> ORGANISM: Artificial Sequence
<220> FEATURE:
<223> OTHER INFORMATION: primers directed to human genes

<400> SEQUENCE: 3
gccgccttta actggagcaa                                            20

<210> SEQ ID NO 4

```
<211> LENGTH: 21
<212> TYPE: DNA
<213> ORGANISM: Artificial Sequence
<220> FEATURE:
<223> OTHER INFORMATION: primers directed to human genes

<400> SEQUENCE: 4
gcgccaccac agccaactat g                                          21

<210> SEQ ID NO 5
<211> LENGTH: 25
<212> TYPE: DNA
<213> ORGANISM: Artificial Sequence
<220> FEATURE:
<223> OTHER INFORMATION: primers directed to human genes

<400> SEQUENCE: 5
tcccaggaat tggtgataaa gtaga                                      25

<210> SEQ ID NO 6
<211> LENGTH: 21
<212> TYPE: DNA
<213> ORGANISM: Artificial Sequence
<220> FEATURE:
<223> OTHER INFORMATION: primers directed to human genes

<400> SEQUENCE: 6
gataatccgc attcagttgt c                                          21

<210> SEQ ID NO 7
<211> LENGTH: 19
<212> TYPE: DNA
<213> ORGANISM: Artificial Sequence
<220> FEATURE:
<223> OTHER INFORMATION: primers directed to human genes

<400> SEQUENCE: 7
tggttgtaca gggccagga                                             19

<210> SEQ ID NO 8
<211> LENGTH: 20
<212> TYPE: DNA
<213> ORGANISM: Artificial Sequence
<220> FEATURE:
<223> OTHER INFORMATION: primers directed to human genes

<400> SEQUENCE: 8
ggtgtgggtg aggagcacat                                            20

<210> SEQ ID NO 9
<211> LENGTH: 20
<212> TYPE: DNA
<213> ORGANISM: Artificial Sequence
<220> FEATURE:
<223> OTHER INFORMATION: primers directed to human genes

<400> SEQUENCE: 9
ttccaggcat ctgcgatgag                                            20

<210> SEQ ID NO 10
<211> LENGTH: 24
<212> TYPE: DNA
<213> ORGANISM: Artificial Sequence
<220> FEATURE:
<223> OTHER INFORMATION: primers directed to human genes

<400> SEQUENCE: 10
```

```
tggatgccgt ctatgtcgtc ttta                                          24

<210> SEQ ID NO 11
<211> LENGTH: 20
<212> TYPE: DNA
<213> ORGANISM: Artificial Sequence
<220> FEATURE:
<223> OTHER INFORMATION: primers directed to human genes

<400> SEQUENCE: 11
ctggcatgac gcgaacaata                                               20

<210> SEQ ID NO 12
<211> LENGTH: 21
<212> TYPE: DNA
<213> ORGANISM: Artificial Sequence
<220> FEATURE:
<223> OTHER INFORMATION: primers directed to human genes

<400> SEQUENCE: 12
taacatcata agcacctgga g                                             21
```

CYTOMIMETIC FORMULATIONS AND METHODS OF MANUFACTURING THE SAME

CROSS-REFERENCE TO RELATED APPLICATIONS

This application claims benefit of U.S. Provisional Application No. 62/436,698, filed Dec. 20, 2016, the contents of which are hereby incorporated by reference.

FIELD OF INVENTION

The present invention generally relates to novel products useful for skin and hair care, and a method of manufacturing the same.

BACKGROUND

The intracellular environment in the skin plays a key role on the quality of this tissue, affecting the vitality, mobility and ability to repair the local cell populations. The development of cosmeceuticals capable of mimicking the biological properties of the skin extracellular matrix (ECM) is a strategic objective to combat the aging processes. Success can be ascertained by restoring functionality of the local cell populations. Due to consumer preferences for natural or nature-based products, a cosmeceutical with nature-based actives that can effectively combat the appearance of skin aging processes is a desirable goal. The current art is limited in this respect, and alternative and more effective products are sought.

SUMMARY OF THE INVENTION

The present invention generally relates to novel products useful for skin and hair care, and methods of manufacturing the same. A benefit of these products is that they can effectively combat the appearance of skin aging processes.

Herein, the inventors provide cytomimetic formulations made using active ingredients derived and/or modified from natural sources, such as fermented truffle extract, hyaluronic acids of different molecular weight (Mw), olive leaf extract in thermal water and fermented must of Falernum grapes. These cytomimetic formulations provide the desired cosmeceutical characteristics to combat the appearance of skin aging processes. Moreover, the relevant actives have different properties than when used individually, and are characterized by an unpredictable strong synergy of action when used together.

In embodiments, a cytomimetic formulation is provided comprising at least two of: (a) a fermented truffle extract; (b) a plurality of hyaluronic acids of different molecular weight, ranging from 50 KDa up to 2000 KDa; (c) an olive leaf extract in a mineral-containing water; and (d) a fermented grape must. In embodiments, the cytomimetic formulation is a cosmetic formulation. As used herein, a cytomimetic formulation is a formulation containing cosmetically active ingredients.

In embodiments, a cosmetic formulation is provided as recited hereinabove further comprising at least one of: (a) an aqueous phase; (b) an oil phase; (c) one or more preservatives; and (d) one or more fragrances.

In embodiments, a method is provided for manufacturing a cosmeceutic comprising admixing the cytomimetic formulation as recited hereinabove with a carrier suitable for topical administration.

In embodiments, a method of eliciting or enhancing one or more of cell growth, skin rejuvenation, counteraction of one or more features of skin aging and promotion of skin tissue wound repair, is provided comprising applying an amount of a cytomimetic formulation as recited herein to human skin effective to elicit or enhance one or more of cell growth, skin rejuvenation, counteract of one or more features of skin aging, or promote skin tissue wound repair.

In embodiments, a product is provided comprising fermented truffle extract obtained by a process comprising the following steps: (a) homogenizing a truffle tuber in a physiological solution to form a homogenate; (b) fermenting with one or more microorganisms the homogenate to form a fermentate; (c) filtering the fermentate to remove particulate matters to form a filtered fermentate; (e) drying filtered fermentate by lyophilization or spray drying so as to obtain a dry fermented truffle extract.

In embodiments, a product is provided comprising olive leaf extract obtained by a process comprising the steps of: (a) homogenizing fresh olive leaves in mineral-containing water form a homogenate; (b) extracting the homogenate for a predetermined period of time to form an extract; and (c) filtering the extract to remove solid particulate matters, so as to obtain the olive leaf extract.

In embodiments, a product is provided comprising fermented grape must obtained by a process comprising the steps of: (a) obtaining freshly harvested grapes; (b) recovering grape juice from the grapes by mechanical pressure; (c) fermenting the grape juice to form a fermentate; (d) filtering the fermentate to remove particulate so as to obtain a clear solution; and (e) drying the clear solution by lyophilization or spray drying, so as to obtain dry fermented grape must.

In embodiments, a method is provided of inducing expression of a heat shock protein in a skin cell comprising adminstering a cytomimetic formulation as described herein comprising a fermented truffle extract in an amount effective to induce expression of a heat shock protein in a skin cell.

BRIEF DESCRIPTION OF THE FIGURES

Exemplary embodiments of the present invention will be described with reference to the accompanying figures, wherein.

DETAILED DESCRIPTION

Figure 1:
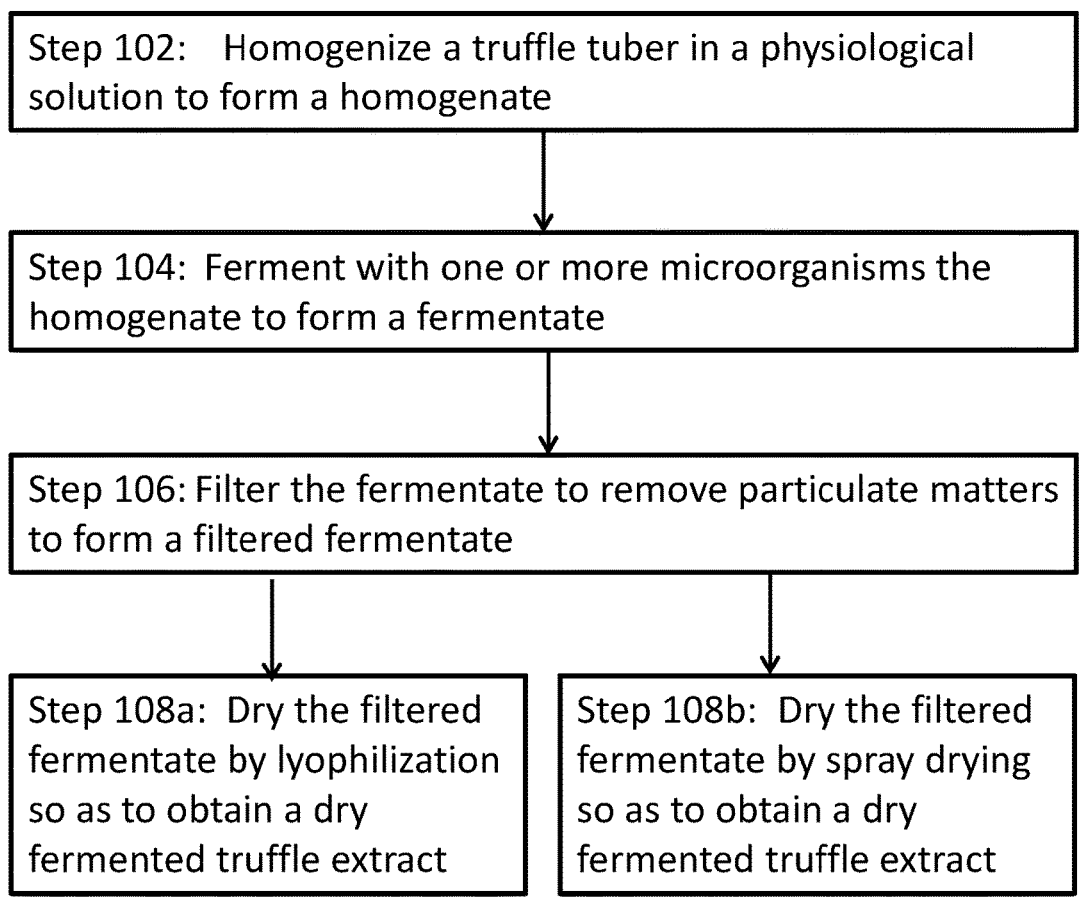
FIG. 1: A flowchart showing an exemplary process for producing fermented truffle extract. Suitable muicroorganism include *Saccharomyces cerevisiae*.
Figure 2:
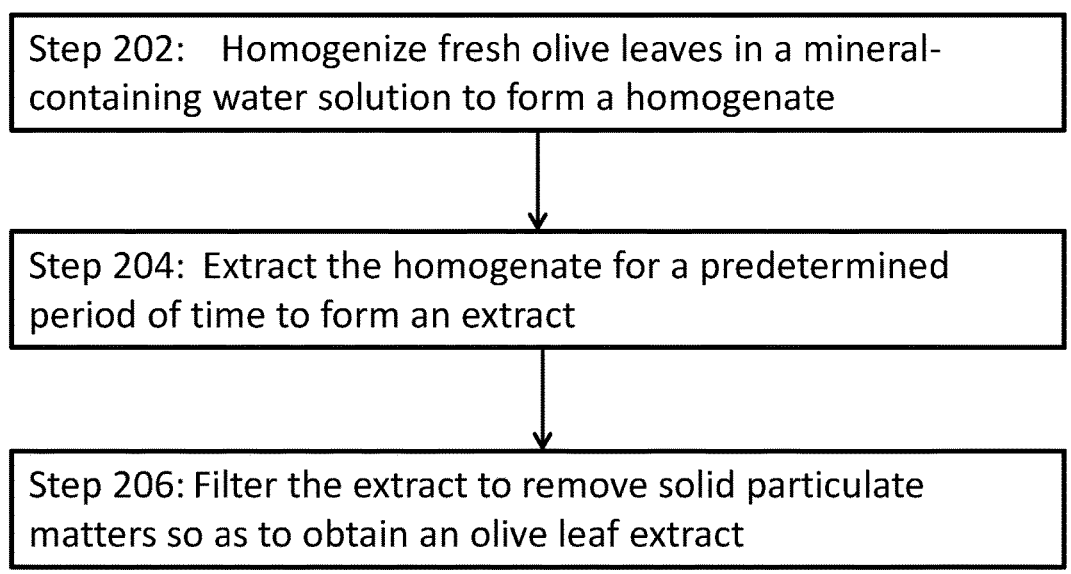
FIG. 2: A flowchart showing an exemplary process for producing Olive leaf extract.
Figure 3:
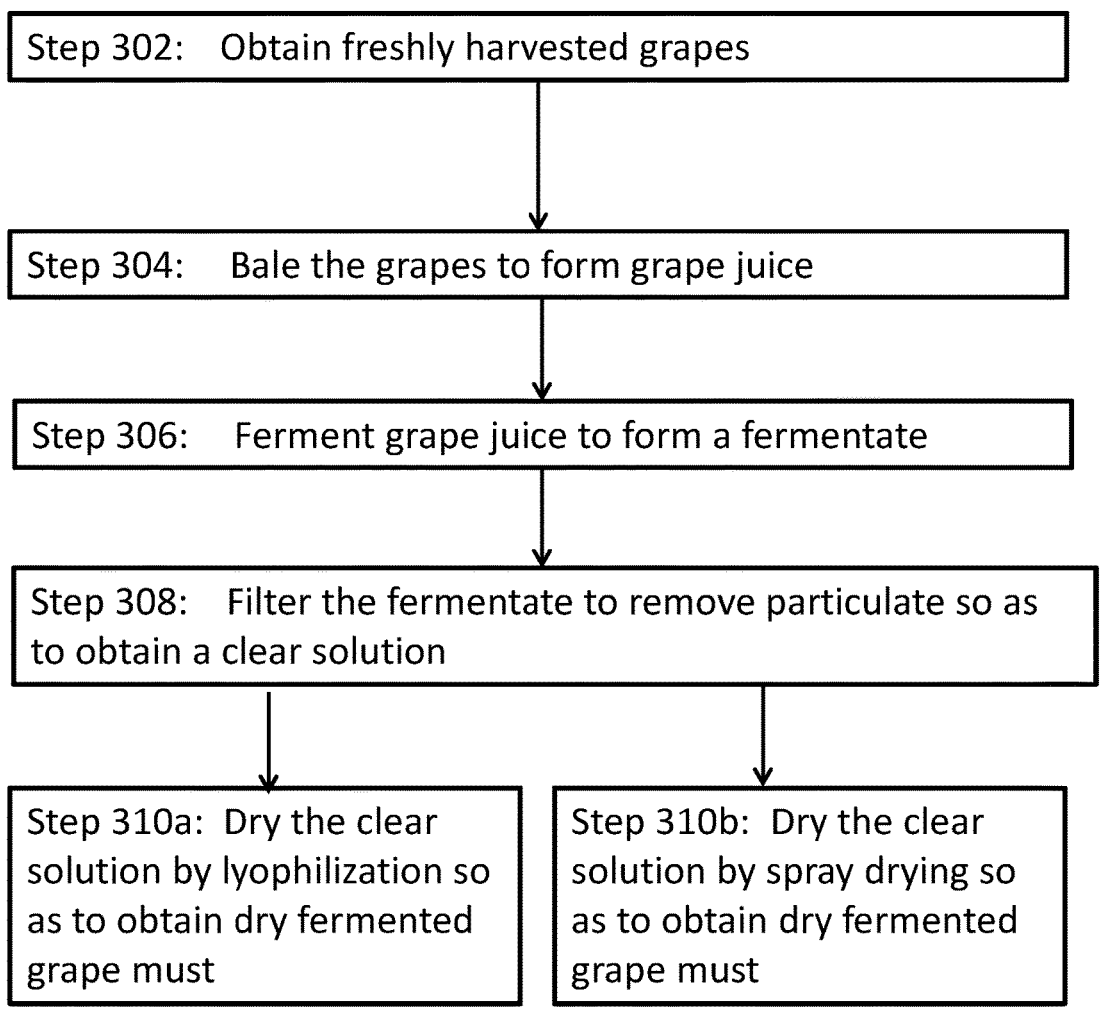
FIG. 3: A flowchart showing an exemplary process for producing fermented grape must.

The present invention generally relates to an improved cosmetic formulation comprising at least two of various ingredients derived from natural sources, which when combined provide a synergistic effect on combating aging processes in skin. Signficantly, the ingredients are modified in a manner not present in nature and/or are combined into a product which shows synergistic effects not seen in indivdual components alone. These cosmetic formulations are cytomimetic, and provide very desirable cosmeceutical characteristics to combat the appearance of skin aging processes.

In embodiments, a formulation of cosmetically active components, a cytomimetic formulation, is provided comprising two or more of: (1) a fermented truffle extract, (2) a hyaluronic acid, (3) an olive leaf extract in a mineral-containing water, and (4) a fermented grape must.

In embodiments, a cytomimetic formulation is provided comprising at least two of: (a) a fermented truffle extract; (b) a plurality of hyaluronic acids of different molecular weight, ranging from 50 KDa up to 2000 KDa; (c) an olive leaf extract in a mineral-containing water; and (d) a fermented grape must.

In embodiments, a cytomimetic formulation is provided comprising: (a) a fermented truffle extract comprising 1-30% total weight of active ingredients; (b) a plurality of hyaluronic acids of different molecular weight, ranging from 50 KDa up to 2000 Kda, comprising 20-60% of total weight of active ingredients; (c) an olive leaf extract in a mineral-containing water, comprising 10-30% total weight of active ingredients; and (d) a fermented grape must, comprising 10-60% total weight of active ingredients.

In embodiments, a cosmetic formulation is provided comprising: (a) a fermented truffle extract comprising 1-30% total weight of the cosmetic formulation; (b) a plurality of hyaluronic acids of different molecular weight, ranging from 50 KDa up to 2000 Kda, comprising 20-60% of total weight of the cosmetic formulation; (c) an olive leaf extract in a mineral-containing water, comprising 10-30% total weight of the cosmetic formulation; and (d) a fermented grape must, comprising 10-60% total weight of the cosmetic formulation.

In embodiments, the cytomimetic formulation further comprises (e) a carrier suitable for topical application to human skin. In embodiments, the cytomimetic formulation further comprising (e) a carrier suitable for topical application to human skin is a cosmetic formulation. Examples of carriers suitable for topical adminstration include, creams, ointments, pastes, gels, solutions, lotions, suspension concentrates, suspoemulsions niosomes, liposomes, microemulsions, and liposheres, to name a few.

In embodiments, the cosmetic formulation, when applied to human skin, elicits or enhances at least one of: (i) cell growth, (ii) skin rejuvenation, (iii) counteraction of one or more features of skin aging, and (iv) skin tissue wound repair.

In embodiments, the cosmetic formulation when applied to human skin elicits or enhances skin rejuvenation in reducing scaliness (and/or improves skin hydration) versus skin not treated with the actives.

In embodiments, the cosmetic formulation when applied to human skin elicits or enhances skin rejuvenation by decreasing sebum secretion of oily skin relative to untreated oily skin.

In embodiments, the cosmetic formulation when applied to human skin elicits or enhances skin rejuvenation by increasing sebum secretion of dry skin relative to untreated dry skin.

In embodiments, the cosmetic formulation when applied to human skin elicits or enhances counteraction of one or more features of skin aging by improving skin elasticity relative to untreated skin.

In embodiments, the cosmetic formulation when applied to human skin elicits or enhances counteraction of one or more features of skin aging by reducing skin wrinkles relative to untreated skin. In embodiments, the cosmetic formulation when applied to human skin elicits or enhances counteraction of one or more features of skin aging by reducing roughness of the skin relative to untreated skin.

In embodiments, the cosmetic formulation when applied to human skin elicits or enhances skin tissue wound repair by reducing the skin wound repair time relative to untreated skin.

In embodiments, the cytomimetic formulation comprises fermented truffle extract and the fermented truffle extract is obtained by a process comprising the following steps: (a) homogenizing a truffle tuber in a physiological solution to form a homogenate; (b) fermenting with one or more microorganisms the homogenate to form a fermentate; (c) filtering the fermentate to remove particulate matters to form a filtered fermentate; (e) drying filtered fermentate by lyophilization or spray drying so as to obtain a dry fermented truffle extract.

In embodiments, the truffle tuber is homogenized in 0.1M sodium phosphate buffer, at pH 5-7 for 1 h, and at 3000-6000 rpm.

In embodiments, the homogenate is fermented for about 24 h at a temperature of 25-30° C., and at a pH 5-7, with a flux of sterile air of 1.5-2.5 L/min. In embodiments, the fermentate is filtered through a 1 micron filter, then followed by 0.45 micron filter, then followed by a 0.22 micron filter, so as to produce the filtered fermentate.

In embodiments, the truffle tuber is a *Tuber magnatum*. In embodiments, the truffle tuber is a *Tuber magnatum preciosa*.

In embodiments, the one or more microrganism comprises *Saccharomyces cerevisiae*.

In embodiments, the cytomimetic formulation comprises the plurality of hyaluronic acids of different molecular weight, comprises hyaluronic acids of 1800 KDa, 800 KDa and 200 KDa.

In embodiments, the hyaluronic acids of 1800 KDa, 800 KDa and 200 KDa are present, each in a proportion of not less than 2% of the total weight of hyaluronic acids present.

In embodiments, the hyaluronic acids of 1800 KDa, 800 KDa and 200 KDa are present at a 33.3% by weight relative ratio of the total weight of hyaluronic acids present.

In embodiments, the cytomimetic formulation comprises olive leaf extract and the olive leaf extract is obtained by a process comprising the steps of: (a) homogenizing fresh olive leaves in mineral-containing water solution to form a homogenate; (b) extracting the homogenate for a predetermined period of time to form an extract; and (c) filtering the extract to remove solid particulate matters, so as to obtain the olive leaf extract.

In embodiments, the mineral water is a thermal water obtained from Thurio Spring at Spezzano Thermal Baths, Calabria, Italy.

In embodiments, the solid/solvent ratio during extraction is 1 to 4 ratio in weight and the extraction time is 24-72 hours at 4° C. and pH 7.

In embodiments, the solid/solvent ratio during extraction is 1 to 4 ratio in weight and the extraction time is 24 hours at 4° C. and pH 7.

In embodiments, the cytomimetic formulation comprises fermented grape must and the fermented grape must is obtained by a process comprising the steps of: (a) obtaining freshly harvested grapes; (b) recovering grape juice from the grapes by mechanical pressure; (c) fermenting the grape juice to form a fermentate; (d) filtering the fermentate to remove particulate so as to obtain a clear solution; and (e) drying the clear solution by lyophilization or spray drying, so as to obtain dry fermented grape must.

In embodiments, the grapes are Aglianic grapes from the slopes of Mount Falernus, Italy.

In embodiments, the fermentation is performed at 10-15° C. for 24-48 hours. In embodiments, the fermentation is performed at 10-15° C. for 24 hours.

In embodiments, the cytomimetic formulation is a cosmetic formulation. In embodiments, the cosmetic formulation comprises from 0.1 to 50% w/w of the cytomimetic formulation.

In embodiments, a cosmetic formulation is provided as recited hereinabove further comprising at least one of: (a) an aqueous phase; (b) an oil phase; (c) one or more preservatives; and (d) one or more fragrances.

In embodiments, the cosmetic formulation comprises an aqueous phase. In embodiments, the aqueous phase comprises at least one of: (i) water, (ii) glycerin, (iii) glyceryl polyacrylate, (iv) acrylates copolymer, (v) butylene glycol, (vi) carbomer, and (vii) xanthan gum.

In embodiments, the cosmetic formulation comprises an oil phase. In embodiments, the oil phase comprises at least one of: (i) *Olea europaea* fruit oil; (ii) stearoxymethicone/dimethicone copolymer; (iii) polymethylsilsesquioxane; (iv) polyacrylate-13; (v) HDI/trimethylol hexyllactone crosspolymer; (vi) polyisobutene; (vii) cholesteryl nonanoate; (viii) hydrogenated lecithin; (ix) polysorbate 20; (x) cholesteryl chloride; (xi) sodium acrylates copolymer; (xii) cholesteryl oleyl carbonate; (xiii) silica; and (xiv) methyl methacrylate crosspolymer.

In embodiments, the cosmetic formulation comprises one or more preservatives. In embodiments, the one or more preservatives comprises at least one of: (a) phenoxyethanol; and (b) ethylhexylglycerin.

In embodiments, the cosmetic formulation comprises one or more fragrances.

In embodiments, the cosmetic formulation comprises each of: (a) an aqueous phase; (b) an oil phase; (c) one or more preservatives; and (d) one or more fragrances.

In embodiments, the cosmetic formulation is a skincare formulation, a hair product, a scalp product, or a makeup formulation.

In embodiments, a method is provided for manufacturing a cosmeceutic comprising admixing the cytomimetic formulation as recited hereinabove with a carrier suitable for topical administration.

In embodiments, a method of eliciting or enhancing one or more of cell growth, skin rejuvenation, counteraction of one or more features of skin aging and promotion of skin tissue wound repair is provided comprising applying an amount of a cytomimetic formulation as recited herein to human skin effective to elicit or enhance one or more of cell growth, skin rejuvenation, counteract of one or more features of skin aging, or promote skin tissue wound repair.

In embodiments, a product is provided comprising fermented truffle extract obtained by a process comprising the following steps: (a) homogenizing a truffle tuber in a physiological solution to form a homogenate; (b) fermenting with one or more microorganisms the homogenate to form a fermentate; (c) filtering the fermentate to remove particulate matters to form a filtered fermentate; (e) drying filtered fermentate by lyophilization or spray drying so as to obtain a dry fermented truffle extract.

In embodiments, a product is provided comprising olive leaf extract obtained by a process comprising the steps of: (a) homogenizing fresh olive leaves in mineral-containing water form a homogenate; (b) extracting the homogenate for a predetermined period of time to form an extract; and (c) filtering the extract to remove solid particulate matters, so as to obtain the olive leaf extract.

In embodiments, a product is provided comprising fermented grape must obtained by a process comprising the steps of: (a) obtaining freshly harvested grapes; (b) recovering grape juice from the grapes by mechnical pressure; (c) fermenting the grape juice to form a fermentate; (d) filtering the fermentate to remove particulate so as to obtain a clear solution; and (e) drying the clear solution by lyophilization or spray drying, so as to obtain dry fermented grape must.

In embodiments, the cosmetic formulation is in the form of one of the following: a cream, a lotion, a gel, an ointment, a macro-emulsion, a micro-emulsion, a nano-emulsion, a serum, a solution, a balm, a patch, a microneedle patch, a skin delivery enhancing system, or a mask.

In embodiments, cosmetic formulations may include those for skin (including, in embodiments, day-cream, night cream, anti-aging product, skin rejuvenating product, skin conditioner, moisturizer, sun protecting gel, sun protecting cream, brightening cream, after-sun product, mask, body lotion, shower gel, and soap).

In embodiments, cosmetic formulations may include those for skin hair or scalp (including, in embodiments, mask, conditioner, shampoo, and lotion).

In embodiments, cosmetic formulations may include those for makeup (lipstick, foundations, lip gloss, lip balm, rouge).

In embodiments, the formulations can be suitable for treatment of healthy, young, old, aged, damaged, photo-damaged, wrinkled, irritated, acne, age spotted, or stretch marked skin.

In embodiments, the formulation may be suitable for treatment of skin previously treated with cosmetic products, or treated with cosmetic procedures.

In embodiments, the formulations may be suitable for treatment of healthy, damaged, gray, or dyed hair.

In embodiments, the formulations can be suitable for treatment of healthy or damaged scalp.

In embodiments, a cytomimetic formulation is provided comprising one or more of a fermented truffle extract, a hyaluronic acid, an olive leaf extract in a mineral-containing water, and a fermented grape must.

In embodiments, a method is provided for manufacturing a cosmeceutic comprising admixing the cytomimetic formulation as described herein with a carrier suitable for topical adminstration.

In embodiments, a method is provided for eliciting or enhancing one or more of cell growth, skin rejuvenation, counteraction of one or more features of skin aging and promotion of skin tissue wound repair, comprising applying an amount of a formulation as recited herein to human skin effective to elicit or enhance one or more of cell growth, skin rejuvenation, counteract of one or more features of skin aging, or promote skin tissue wound repair.

In embodiments, a method is provided for eliciting or enhancing one or more of cell growth, skin rejuvenation, counteraction of one or more features of skin aging and promotion of skin tissue wound repair, comprising applying an amount of the formulation as recited herein to human skin effective to elicit or enhance one or more of cell growth, skin rejuvenation, counteract of one or more features of skin aging, or promote skin tissue wound repair.

In embodiments, a product is provided comprising fermented truffle extract obtained by a process comprising: a) homogenizing a truffle tuber in a physiological solution; b) subjecting the homogenate to a fermentation with one or more microorganisms; c) removing particulate by filtration of fermentate; drying filtered fermentate solution by lyophilization or spray drying so as to obtain a dry fermented truffle extract.

In embodiments, a product is provided comprising olive leaf extract obtained by a process comprising: a) homogenizing fresh olive leaves in mineral-containing water; b) permitting the homogenate to extract; c) removing solid particulate by filtration, so as to obtain the olive leaf extract.

In embodiments, a product is provided comprising fermented grape must obtained by a process comprising a) obtaining freshly harvested grapes; b) recovering grape juice from the grapes by mechanical pressure; c) fermenting grape juice from the grapes; d) removing particulate of the fermentate by filtration so as to obtain a clear solution; and e) drying the clear solution by lyophilization or spray drying, so as to obtain dry fermented grape must.

In embodiments, a method is provided of inducing expression of a heat shock protein in a skin cell comprising adminstering a cytomimetic formulation as described herein comprising a fermented truffle extract in an amount effective to induce expression of a heat shock protein in a skin cell. In embodiments, the heat shock protein is HSP 70 or HSP 90. In embodiments, adminstering the cytomimetic formulation induces expression of both a HSP 70 and a HSP 90 in a skin cell.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention. Thus, a molecule which is 200 KDa to 800 KDa includes, unless otherwise stated, molecules of 201 KDa, 202 KDa, 203 KDa etc. Thus, a percentage range of 10-30% includes, unless otherwise stated, percentage ranges of 10-25%, 12-30%, etc. as well as the indivdual percentages of 11%, 15%, 20% etc.

This invention will be better understood from the Experimental Details, which follow. However, one skilled in the art will readily appreciate that the specific methods and results discussed are merely illustrative of the invention as described more fully in the claims that follow thereafter.

Active Ingredients

The development of cosmeceuticals capable of mimicking the biological properties of the extracellular matrix (ECM) present in the skin tissue is a strategic objective to counteract aging and stress effects by restoring the optimal functionality of the resident cell populations.

Cytomimetic technology, in the formulations disclosed herein, mimics healthy, vital parts of the skin tissue environment where skin cells thrive. Using this mimicry it effectively infuses the skin tissue (ECM) with special, luxurious ingredients to balance, tone and beautify. This proprietary technology enhances biological activity by mimicking parts of the macromolecular universe that exist in our skin.

Cytomimetic formulations, that employ the actives of fermented truffle extracts, HA of different Mw, olive leaf extract in thermal water, Falernum fermented grapes, have surprisingly be shown by the inventors to possess a strong synergism amongst themselves. The effectiveness of these naturally-based active ingredients are enhanced when used together, by mimicking the complex actions of bio-stimulation, signaling, repair and protection of their own fully functional ECM. Below, the basis of each individual actives component is discussed.

Truffle Fermented Extract—

Truffles have a number of biological activities, such as antioxidant, antiviral, anti-microbial, hepatoprotective, anti-mutagenic, anti-inflammatory, anti-carcinogenic, and are anti-tuberculoid. (N. Beara et al./Food Chemistry 165 (2014) 460-466). One of the most promising truffles, from a biochemical point of view, is *Tuber magnatum preciosa*. It is native to Italy, namely the Piedmont, Tuscany and Emilia Romagna regions. The effects of truffle oil aroma are confirmed by the ability of some scent molecules to interact with receptors and trigger some significant signals in human cells. The challenge has been trying achieve the relevant effects on the skin for cosmetic purposes. Results herein demonstrate that fermented truffle extracts contain one or more substances, that with a synergistic action, induce the heat shock response, eliciting quantifiable beneficial effects on cells.

Surprisingly the inventors have found that by subjecting it to a biotransformation/fermentation process, truffle homogenate shows improved biological properties, as empirically demonstred by in vitro keratinocytes and fibroblasts scratch assay with time lapse microscopy (TLVM) (see Table 1) and by the appearance of new activities that are not present in the simple aqueous extract, such as the property of stimulating a response to shock in the cell culture.

The basis of the preservation of the chemical architecture and of the functional properties of a cell organism under stressful conditions is called homeostasis. A feature of homeostasis is the rapid reaction to stressful conditions by expressing genes, whose products and heat shock proteins are specifically dedicated to function against the stress, while also protecting the cellular components (Lindquist S., 1986, Ann Rev Biochem, 55,1151-1191; Morimoto, R. I. 1993, Science, 259: 1409-1410; Morimoto, R. I., et al., 1990, In Stress proteins in biology and medicine pp. 1-36. Cold Spring Harbor Laboratory Press, Cold Spring Harbor, N.Y.).

The response to shocks and, in particular, the heat shock response (HSR), is an ancient and highly conserved cytoprotective mechanism and the heat shock proteins (HSPs) are among the most abundant proteins in the biosphere. The fact that they show such remarkable evolutionary conservation, suggests they are essential for basic cellular function.

A number of studies have shown that the expression of these proteins has a close relationship with life history, exerting influence on biological phenomena such as stress resistance (Morimoto, R. I. and Santoro M. G., 1998, Nature Biotech, 16:833-838.), aging and longevity (Tao D, Lu J, et al. 2004, Acta Biochim Biophys Sin (Shanghai), 36:618-22; Calderwood S K, et al., 2009, Gerontology; 55:550-558).

The heat shock response mechanism for cell protection against stress results in the down-regulation of many genes and the activation of others, whose main function is to help the cell survive. The production of heat shock proteins, including protein chaperones, is essential for the folding, repair and recovery of damaged proteins, since it promotes cellular viability under conditions that would otherwise induce cells death (apoptosis).

During the aging process the cell reduces its capacity to synthesize the proper amounts of heat shock proteins under stressful conditions. It is this impairment that may be one of the main factors that contributes to a reduced capacity to maintain homeostasis, and is thus a culprit of damage to the cells.

Among the heat shock proteins, chaperonins are one of the most important classes, since they prevent the incorrect association within and between polypeptide chains during the folding of newly synthesized proteins, while also protecting the pre-existing proteins under cellular stresses. Chaperonins also function in the absence of stress, namely under normal physiological conditions, helping cellular proteins to fold correctly during synthesis on the ribosome. HSP 70 is one of the most studied chaperonins.

It is this mechanism that allows the cell to react to external stress. There is strong consideration that the cell membrane bilayer has fluidity properties that permit sensing of changes in temperature, pH, osmotic and atmospheric pressure, etc. In this respect the cellular membrane may be considered the key sensor of the cell in regards to external stress factors. In fact, following a temperature change, cells compensate for stress induced disturbances, through physiological and biochemical mechanisms of homeoviscous adaptation (Vigh, L., et al., 1998, TIBS 40323: 369-374).

In addition, there is evidence that membrane lipids may participate as molecular chaperones in the folding and possibly in the unfolding of integral membrane proteins. Furthermore, the modification of membrane's physical state influences the expression of heat-shock genes, simulating a heat shock condition. Such an outcome can be caused by some pathological conditions or by the interaction of the membrane with several molecules.

With particular regard to the skin cells (Maytin, E V., 1995, J. Invest. Dermatol 104:448-455; Edwards M J, et al., 1991, J Invest Dermatol 96:392-6; Trautinger F, et al., 1995, Br J Dermatol, 133:194-202; Roh B H, 2008, Ann Dermatol 20:184-9) both dermis and epidermis, expression of HSPs confers resistance to damage caused by stressors, for instance, sunlight exposure. Maytin (Maytin, E V., 1995, J. Invest. Dermatol, 104:448-455) has reported that heat shock proteins play a general role in the protection of the skin from environmental stressors, but also participate in the prevention and repair of the damages caused by exposure to light, heat, chemical injuries, and other traumas.

An important feature of heat shock proteins is their role in the cytoprotection and repair of cells and tissues against the deleterious effects of stress and trauma. Overexpression of one or more heat shock protein genes is sufficient to protect against otherwise lethal exposures to heat, cytotoxic drugs, toxins, and tumor necrosis factor-$\alpha$ (Parsell, D. A. and Lindquist, S., 1994, in The biology of heat shock proteins and molecular chaperones. Cold Spring Harbor Laboratory Press, Cold Spring Harbor, N.Y.).

Yeast cells, engineered to overexpress HSP 70 or HSP 104 cross-protect against lethal heat shock, $H_2O_2$ heavy metals, arsenite, anoxia, and ethanol toxicity. In vertebrates, modulation of the heat shock response or the expression of specific heat shock proteins can either limit or prevent the pathology associated with certain chronic diseases.

It is desirable, from a practical point of view, to obtain naturally derived compounds able to induce the stress response in the cells in the absence of stress. These compounds could create a preventive/defensive strategy in the cells, by mimicking the effects of stress, in turn helping the cells throughout the aging process.

In embodiments, an objective of the present invention is to develop new classes of molecules able to mimic or activate some fundamental process of life. Attention has been spent on repair mechanisms, which make it possible for the cells to survive, since these biological strategies have represented the optimal results of the evolution process for billions of years. There are many compounds capable of increasing the expression of HSPs but the majority of these inducers exhibit significant cytotoxicity.

To cope with increased demand of multifunctional cosmetic products, the induction of HSPs by natural, not toxic compounds, come with excellent prospects.

Herein, the inventors have identified as most representative species of HSP, the 90 and 70, representing the most ubiquitously expressed heat shock proteins, have been taken into consideration. These proteins represent 1-2% of the proteins present in the eukaryotic cells, and are capable of reaching concentrations of 4-6% in the presence of stress.

The studies conducted by inventors on the effects of truffle fermented extracts concentration on cell culture (see Table 2) show a progressive increase of HSP 70 and HSP 90 level of expression with no toxicity. This suggests that truffle fermented extracts contain one or more substances, that with a synergic action, induce the heat shock response, eliciting all the above described beneficial effects on cells.

The discovery of new molecules that are able to activate the stress response, by mimicking the effect of stressors, either in the complete absence of stress or at a lower threshold of stressful conditions, as is the case of fermented truffle extract, represents an important target in this innovative approach, since the knowledge accumulated on this mechanism makes for the possibility of developing innovative strategies for its use to solve cosmetic problems in regards to skin aging (Cf Jindal S, 1996, Trends Bioch. Sci 14:17-20; Magalhaes W V et al. 2012, Eur J Dermat, 22(1) 8-13).

An in vitro test was specifically used by the inventors to assess the antioxidant activity on fermented and non-fermented truffle extract (Table 3). Human keratinocytes and fibroblasts treated with $H_2O_2$ or exposed to UV-A radiation show an increased lipid peroxidation that was significantly reduced either by treating the cells with fermented truffle extract after the stress or before it.

Hyaluronic Acid—

In the development of innovative cosmeceutics for skin biorevitalization there is growing interest in the use of mixtures of HAs with different Mw, with optimized rheological and biological properties. Results herein show the efficacy of different sized HA to stimulate the migration of keratinocytes and fibroblasts. In particular, the data showed that HA 1800 KDa, its intermediate fragments (800 and 200 KDa) and their mixtures increased the repair/remodeling process and fastened the cell migration, confirming in particular the efficacy of HA mixtures in biorevitalizing effect.

Hyaluronic acid, also generically indicated together with its salts as hyaluronans (HA), is a polysaccharide with a linear chain, negatively charged, composed by the repetition of n disaccharide units (-4GlcUA$\beta$1-3GlcNAc$\beta$1-), wherein the D-glucuronic acid (GlcUA) and N-acetyl-D-glucosamine (GlcNAc), are linked by alternating $\beta$-1,3 and $\beta$-1,4 glycosidic bonds. HA is a polysaccharide highly soluble in water and solutions of HA show a visco-elastic behavior of non-newtonian type. These properties are function of: Mw, (and being HA a linear polymer, the chain length), concentration and external environmental conditions, such as pH and ionic strength. HA has a number of unique properties, shown below, making it one of the most versatile and interesting biomaterials:

a) Hydrophilicity and rheological properties of HA: In aqueous solution the molecules of HA entrap large quantities of water (about 1000 times the weight of the HA) taking the form of extended spirals, stabilized by hydrogen bonding between the hydroxyl groups along the chain. These chains will envelop between them, even at very low concentrations, for this, even very dilute, HA solutions have high viscosity, but depend on sliding speed.

b) Lubricating properties of HA: Extraordinary rheological properties of HA solutions make this compound an ideal candidate as a lubricant in the biological field. This is, in fact, one of the actions to which the HA performs in organisms. The joints of our body are an example of this type of behavior.

More than 50% of HA is present in the skin tissue (Laurent T C and Fraser J R., 1992, Faseb J; Oh E J, et al., 2010, J Control Release 141:2; Juhlin L. 1997, J Intern Med, 242:61). Despite the high molecular weight and hydrophilicity of HA, it is known to be delivered through the skin tissue in both mouse and human (Brown T J, et al., 1999 J Invest Dermatol, 113:740; Brown M B and Jones S A. 2005 J Eur Acad Dermatol Venerol, 19:308). The mechanism for transdermal transport of HA has not been clearly veried yet, but there are some possible reasons for the positive effect of HA on transdermal delivery. First, HA is very hygroscopic and can hydrate the stratum corneum enhancing the permeability of the skin. Second, the hydrophobic patch domain in HA chain can enhance the permeability of HA across the stratum corneum. Third, HA receptors distributed in the skin tissue may facilitate the localization of HA in the skin tissue (Brown M B and Jones S A, 2005, J Eur Acad Dermatol Venerol; 19:308; Wang C, et al., 1992 Histochemistry, 98:105; Tammi R et al., 1991, J Invest Dermatol 1991; 97:126). Moreover, it is reported that HA can induce the proliferation, migration, adhesion, and differentiation of keratinocyte (Lokeshwar V B et al., 1996, J Biol Chem, 271:23853; Masellis-Smith A et al., 1996 Blood, 87:1891). HA can also enhance the proliferation of fibroblast through CD44 receptors on the cell membrane (Yoneda M et al., 2004, J Cell Sci, 90:265). For all these reasons HA, despite its size, when applied to the skin, is absorbed and operates as a carrier of other molecules (U.S. Pat. No. 9,220,784 B2, hereby incorporated by reference).

HA is widely distributed in nature. It has been identified in various soft tissues (synovial fluid, skin, umbilical cord, cockscomb, vitreous humor of the eye) and in some prokaryotic cells, in which it creates a mucoid capsule surrounding the cell. In vertebrates the HA has a wide variety of functions: in the skin it ensures tissue hydration; in the cartilage it binds to proteoglycans to adjust the content of water and ions, to stabilize tissue physical properties and cell-substrate interactions. The average molecular weight of the HA of synovial fluid and the umbilical cord is 3,000-4,000 KDa.

The biological responses elicited by the HA depend strongly on its Mw, in particular the accumulation of low Mw HA is an early signal of alteration of the ECM, which activates the shelter responses at tissue level, while a preponderance of high Mw HA signifies a situation of good homeostasis. As a result of its properties and biological functions, HA has a high added value (its market value far exceeds that of other natural polysaccharides), with applications ranging from the medical sector to the cosmetics sector.

In many HA applications, the performance depends on its Mw. For this, the mean molecular weight of the HA and a polydispersion index Mw/Mn (measuring the breadth of the molecular weight distribution curve, where Mn is the number average Mw, defined as the total weight of all the polymer molecules of a sample divided by the total number of molecules, and Mw is the weight average molecular weight, which takes account of the different mass of these molecules) needs to be the gold standard considered during the development and production processes (Camenisch T D et al., 2000, American J. Respiratory Cell and Molecular Biology 23, 431-433, hereby incorporated by reference).

In recent years, scientists have been studying the correlation between HA Mw and physiological functions (Raoudi D. et al., 2008, Wound Repair and Regen, 16(2 Suppl), 274-87; Ke, Sun Qiao, et al., 2011, Food Chem Toxicol., 49(10), 2670-5; Cowman, L et al., 2015 Frontiers in Immunology, 6, 261; Ferguson, R. et al., 2011, Int J Pharm, 420 (1 Suppl), 84-92). Generally, native HAs (Mw ranging from 2000 to 800 KDa) are space-filling molecules with anti-inflammatory and anti-angiogenic effects, while lower Mw HA (Mw<50 KDa) may be involved in a proinflammatory process (Frenkel J. S., 2014, Int Wound J, 11, 159-163). In particular, there has been an increasing effort to clarify the role of HAs in the interaction with the epidermis/dermis tissues (Ghosh, P., & Guidolin, D., 2002, Current Abstracts Seminars in Arthritis and Rheumatism, 32(1), A2-A4). HA has also been reported to be a free radical scavenger, presenting an antioxidant function. It enhances the wound healing process and presents both angiogenic (Gao F. et al., 2010, Matrix Biol., 29(2), 107-16) and immunostimulatory activity (Ke et al., 2011 Food Chem Toxicol., 58, 401-7).

Nevertheless, given HA turnover, all HA fragments have a physiological function, as could be expected, that is often very important in the healing processes, biological tissue homeostasis and biosynthesis of ECM. Native HA is reported to be fragmented in smaller molecules during ECM degradation after acute tissue injury, in order to activate the host innate immune response by recruiting macrophages and other specific cells, to produce chemokines required to begin repair/restoration of tissue integrity.

Due to water-attracting characteristics in tissue repair, for example, long chain HA has cushioning and visco-elastic properties, that create a porous scaffold onto which the cell might migrate; on the contrary, medium-size HA fragments (100-250 kDa) have been found to promote cell migration and contemporarily to stimulate and modulate pro-inflammatory cytokines production; finally very small fragments (4 saccharides) have been found to induce chemotaxis (Frenkel, J. S., 2014, Int Wound J, 11, 159-163.).

Vigetti and collaborators have reported that small HA fragments, ranging from 3 to 25 disaccharides (1.2-10 kDa), have inflammatory effects and show pro-angiogenic activity in human cell models (Vigetti, D., et al., 2014, Biochim Biophys Acta., 1840(8), 2452-9). Relative to this, a recent report has shown that HA fragments stimulate chemokine and cytokine gene expression interacting with TLR-4 (Jiang D et al., Physiological Reviews, Vol. 91 no. 1, 221-264). RHAMM receptor was mainly involved in the cell migration. As a matter of fact, RHAMM-HA interaction does play an important function in tissue injury and repair (Viola et al., 2015, Glycoconj J., 32(3-4), 93-103).

Although sometimes contradictory, the set of knowledge on the differentiated effects of HA as a function of its Mw, is an important premise for the construction of innovative cosmeceuticals, in which the optimization of mixtures of HAs with different Mw allows for the obtainment of effective biological responses in biostimulation processes, to contrast skin aging. In addition, although many reports have confirmed the differences relating to HA Mw, there have been no experimental highlights at the biological level of these different compounds.

Prompted by this knowledge and shared experience of diffused confusion in assessment and in the relationship between HA size and function, the inventors addressed the question through rigorous methods. By identifying an optimal range of HA fragments and their biochemical activities, and by using in vitro models and specific biochemical test, the inventors have elucidated the effect of specific HA fragments and their mixture when they interact with membrane receptors, in modulating cellular biostimulation, wound repair, cell migration, and cytokine expression. Results herein show the efficacy of different sized HA to stimulate the migration of keratinocytes and fibroblasts. In particular, the data showed that HA 1800 KDa, its intermediate fragments (800 and 200 KDa) and their mixtures increased the repair/remodeling process and fastened the cell migration, confirming in particular the efficacy of HA mixtures in biorevitalizing effect.

With acidic hydrolysis in a heterogeneous phase (Melander C. and Tommeraas K., 2010, Carbohydrate Polymers 82, 874-879; hereby incorporated by reference), a full array of HA fragments of different size (Table 4) was obtained, with identical structural disaccharides units, thus ensuring that biochemical and biological outcomes are not ascribed to a HA modified chemical structure. $^1$H-NMR analysis confirmed these results. The structural and rheological data (Viscotek analysis) confirmed that products are similar to the ones obtained by hyaluronidase in vivo and, for this purpose, suitable to be tested for in vitro biological response.

To elucidate the biological roles of HA fragments by studying specific biomarkers from the preliminary phases of wound healing process, an in vitro scratch test has been used with TLVM (D'Agostino et al., 2015, BMC cell biology, 16:19, hereby incorporated by reference) on human keratinocytes and fibroblasts. The highest Mw HA samples led to complete repair in a shorter time; however, all the HA fragments tested enhanced the scratch repair rate compared to the control (Table 5).

Interaction between different sized HA and relative specific receptors was investigated to improve knowledge of the biochemical basis in the activation/silencing of pathways relative to HA and its degraded products in vivo. Results have shown the efficacy of different sized HA to stimulate the migration of keratinocytes and fibroblasts. In particular, the data showed that HA 1800 KDa, its intermediate fragments (800 and 200 KDa) and their mixtures increased the repair/remodeling process and fastened the cell migration, confirming in particular the efficacy of HA mixtures in biorevitalizing effect.

Molecular analysis at gene and protein level corroborated the data derived from time-lapse experiments. HA exerts biological activity thought interaction with its receptors on cell surface; in particular CD44, the main HA receptor, interacting with HA, triggers different biological responses, ranging from cell proliferation and ECM degradation to angiogenesis and inflammation.

All HA analyzed herein activated CD44, but the major responses were found in presence of HA 1800-800 KDa (Table 7). All HA samples increased RHAMM expression, however results were significantly higher for 200 KDa (Table 7).

TLRs are receptors of innate immunity and TLR-2 and TLR-4 may bind HA fragments, inducing signaling. Differently from CD44 response, TLR-4 activity, correlated to inflammatory process, is significantly down-regulated in all HA tested (Table 7). Gene expression data of HA receptors were confirmed by immunostaining.

In order to follow-up the biochemical cascade turned on by HA-receptor interaction, the expression profile of key cytokines possibly involved have been evaluated. The results herein show an up-regulation of TGF β-1 and TNF-α in presence of all HA treatments (Table 7). Therefore, all hyaluronan fragments tested were both safe and biologically active. Furthermore they may support cell activation, therefore helping in skin reparair procedures and biological remodeling.

In consideration of the differentiated biological effects that characterize the HA as a function of its Mw, and of the heterogeneity of the HA molecular population naturally present in the ECM, a cytomimetic formulation was synthesized by mixing HA of different Mw.

The experimental data (Table 5), using the test model of wound healing time lapse microscopy of human chondrocytes and fibroblasts, showed that the best results were obtained using mixtures formed by comparable amounts of HA 1800, 800 and 200 KDa. In fact, the synergism between the biological properties of these different HAs reduced the healing time by 50-70% in both experimental models. An in vitro test was specifically developed to assess the antioxidant activity of the mixture of HAs 1800+800+200 KDa (Table 8). Human keratinocytes and fibroblasts treated with $H_2O_2$ or exposed to UV-A radiation show an increased lipid peroxidation, that was reduced either by treating the cells with HAs 1800+800+200 KDa after the stress or before it.

Olive Leaf Extract in Thermal Water—

Among the active ingredients that have a strategic role to draw cosmeceuticals effective in protecting the skin and preventing skin aging, compounds with antioxidant activity are considered elective. Of particular interest are the natural antioxidants obtained generally by extraction from plant sources. In order to help achieve optimal protective effects as a radical scavenger, it is preferable that there be a mixture of compounds with different spectrums of antioxidant activity. A particularly interesting source of active ingredients with antioxidant activity are Olive leaves (*Olea europaea*). Only fresh leaves were used in the extracts, instead of dried leaves or reconstituted powders. Experimental data herein shows that liquid Olive leaf extract made directly from fresh leaves has a broader spectrum potency than has previously been the case, including a synergistic action with thermal mineral water on wound closure time.

The extract of olive leaves is characterized by the presence of a significant quantity of oleoeuropein (IUPAC name 4S,5E,6S)-4-[2-[2-(3,4-dihydroxyphenyl) ethoxy]-2-oxoethyl]-5-ethylidene-6-[[(2S,3R,4S,5S,6R)-3,4,5-trihydroxy-6-(hydroxymethyl)-2-tetrahydropyranyl]oxy]-4H-pyran-3-carboxylic acid, methyl ester). This composition is accompanied by minor amounts of structurally related polyphenols with antioxidant activity as 10-hydroxyoleuropein, ligstroside, and 10-hydroxyligstroside. Oleuropein had activity as an agonist of the G-protein estrogen receptor (Eric R. et al., 2014, Molecular and Cellular Endocrinology 389 (1-2): 71-83).

The 'natural balance' of antioxidant actives in a fresh Olive leaf extract provides a more powerful free radical scavenging capacity as opposed to when the individual components are isolated. This involves a synergistic action between flavonoids, oleuropeosides and phenols.

Aqueous systems are used when preparing the extract of Olive leaf, leaving the homogenized leaf to extract for 24-48 hours.

A strong innovation in the field of phytoexracts has been the use of thermal water with this special composition and these therapeutic properties as an extraction system. This helps create important synergies between the biological effects of active extracts and those of the extracting system. In this respect, the thermal spring water is of particular interest, including that obtained from the Thurio spring at the Spezzano Thermal Baths in Italy. Thanks to the abundance of peculiar microelements, it is an active principle of choice. These microelements provide outstanding soothing properties. As reported in Table 9, using the in vitro keratinocytes and fibroblasts scratch assay with TLVM, a significant synergism of action between the thermal water and the active present in the olive leaves extract. Its almost half the time of the closure wound.

In vitro testing was used by the inventors to assess the antioxidant activity accomplished from the Olive leaf extract in thermal water (Table 10). Human keratinocytes and fibroblasts treated with $H_2O_2$, or exposed to UV-A radiation, have shown an increased lipid peroxidation. This was reduced by either treating the cells before or after the stress, using Olive leaf extract in thermal water.

Fermented Falernum Grapes—

Falernian wine (Latin Falernum) was historically produced from Aglianico grapes on the slopes of the Falernus mountains, near the border of Latium and Campania region of Italy. Falernian fermented grapes are particularly rich in polyphenols and anthocyanins and provide strong general antioxidant and free radical scavenger activity. However, its antioxidant effects directly on skin cells are not determined. Herein it is shown that Falernian fermented grape must has an important biorevitalizing action (Table 11) and significant antioxidant activity in human skin cells as tested, namely, human keratinocytes and fibroblasts.

The Falernus mountains area is now occupied by the modern day vineyards of Rocca di Mondragone and Mount Massico. Grapes of Falciano del Massico were collected in late August, when they are not yet fully mature. The grapes, after baling and homogenisation, are left to ferment for 48 hours at 10° C., clarified by filtration under pressure and then pasteurized. The ruby liquor that is obtained can be defined as fermented grapes of Falernum. The inventors have determined that this liquor has an important biorevitalizing action (Table 11) and significant antioxidant activity in human skin cells as tested, namely, human keratinocytes and fibroblasts (Table 12). In fact, human keratinocytes and fibroblasts treated with $H_2O_2$, or exposed to UV-A radiation have shown an increased lipid peroxidation that was reduced by either treating the cells before or after the stress with fermented Falernum grape must.

Cytomimetic Formulas and Synergism of their Actives—

The skin extracellular matrix (ECM) develops at the tissue level a series of complex functions indispensable for the correct functionality of the cell population. The realization of a cytomimetic formula for the skin tissue, able to mimic the ECM complex functions, must ensure the tissue biorevitalization, an effective anti-inflammatory/radical scavenger activity and the activation of repair molecular mechanisms.

The inventors have found that by using the natural actives together, a cytomimetic formula was obtained capable of developing the above-described complex functions. The strong synergistic effect between the active employed is absolutely unpredictable. (Fermented truffle extract, mix of HA 1800, 800 and 200 KDa, extract of olive lives in thermal water and fermented Falernum grape must). These are more effective even at extremely low concentrations, rather than employing the various actives individually.

In vitro wound healing experiments (Table 13) have shown that cytomimetic formulas were superior in prompting wound closure. The potent synergism between actives of cytomimetic formula is evident when comparing Examples 1, 5, 9 and 11, with Example 13 in which the actives are present up to three orders of magnitude or less.

In vitro testing was specifically developed to assess the antioxidant activity accomplished by the cytomimetic formulas (Table 14). Human keratinocytes and fibroblasts treated with $H_2O_2$ or exposed to UV-A radiation have shown an increased lipid peroxidation. This was significantly reduced either by treating the cells before or after the stress with cytomimetic formulas.

The potent synergism between actives in the cytomimetic formula is also evident in the production of heath shock proteins, in particular HSP 70 and HSP 90, which gradually increase their expression when the cells are treated with increasing amounts of cytomimetic formula. Table 15, in fact, demostrates the potent synergistic effect of actives present in the cytomimetic formulate that, as reported in the Example 15 are present up to three orders of magnitude in less respect to that reported in Example 3 for the fermented truffle extract alone.

Also analysis of gene expression elicited by Cytomimetic formula in stressful conditions, performed at 0.1 and 0.5%, (Table 16) demonstrated the potent synergistic effect of actives present in this formulae. CD44, RHAMM, TGFβ-1, TNF-α and IL-6 were all up-regulated increasing with cytomimetic formulae concentration, and only TLR-4 activity, correlated to inflammatory process, was significantly down-regulated.

In embodiments of the cosmeceutic products, cytomimetic formulas/fomulations can be used at concentrations ranging from 0.1 to 50% w/w.

To assess the efficacy of a cosmetic composition using cytomimetic formulations, a clinical study was performed on 10 subjects (women), aged between 30 and 54 years, for 28 days. The ingredients of the base composition, and the base composition with a cytomimetic formula are described in Examples 20 and 21.

The efficacy has been proved using instrumental, non-invasive methods: moisture of corneum layer (Corneometry), sebumetry, elasticity and firmness, SELS (Surface Evaluation of Living Skin) parameters: roughness, smoothness, the scaliness degree, wrinkles.

Determination of profilometry (micro-relief). Profilometry was determined instrumentally, by Visioscan VC 98 (Courage+Khazaka electronic GmbH). This testing method is called SELS (Surface Evaluation of the Living Skin) which is based on the graphical illustration of the skin surface under conditions of special illumination and electronic processing of the image, quantified in pixels. "Skin smoothness" (SEsm), can be quantified by finding the average between the depth and width of the skin wrinkles. The smooth skin has a low variation of grey, making the histogram of the level of grey distribution narrow, resulting in a very small SEsm value. "Skin roughness" (SEr), can be demonstrated by using the levels of grey in comparison with the roughness of the entire image. An increased value of this parameter expresses a reduction of the roughness of the analyzed area. "Scaliness" (SEsc) is expressed as the number of pixels whose level of grey is over the threshold limit; the reduction of this parameter is correlated with a low exfoliation of the skin. "Wrinkles" (SEw)—skin wrinkles are calculated from the proportion of horizontal to vertical wrinkles. The value of SEw is higher the more visible the wrinkles are from the point of view of the width and the depth.

Skin elasticity was determined instrumentally (Cutometer MPA 580–Courage+Khazaka electronic GmbH). The elasticity curve obtained by a suction/elongation cycle of the Cutometer, respectively 10 repetitive cycles for the assessment of the area parameter: Among these parameters, in this study the relevant and correlative ones for elasticity and firmness were selected: R2 (Ualufl—gross elasticity, represented by the ratio between the ability of redeformation and final distension, the closer this value is to 1, the more elastic the skin becomes. R5 (Ur/Ue)—net elasticity, the ratio between the immediate retraction and the immediate distension, expresses the ability of the skin recovery after the deformation.

Skin hydration was performed instrumentally, through corneometry, measuring the capacitance. The variations in the dielectric constant is measured by using the water content in the epidermal superficial layer and the level of hydration.

Skin lipid levels in the skin have been quantified using a sebumeter, by measuring the absorbance of a plastic film impregnated with sebum. The film becomes more transparent in the presence of the lipids. The sebum values can be measured between 50-300 μg/cm$^3$.

The clinical results obtained as described in Example 22, show significant improvement of skin physiological parameters after using basic composition with cytomimetic formulate as compared with the base compositions demonstrated in vivo biological effect found in vitro. The results show improvement in all profilometric parameters: reduced scaliness with 116%, improved roughness and smoothness, with 76.6% and, accordingly 47.5% and wrinkle reduction (73.9%). What is very interesting is the balancing effect on lipid content in the stratum corneum. This can be explained by the restoring effect at intercellular level. In the oily skin, the sebum level decreased with 35.67%. The dry skin level increased by 74.30%. In the same time, the base formula using cytomimetic formulate performed a better moisturization (33.33% higher) and an improvement of skin elasticity (R2 40%, R5 50). The comparative performance in vivo (clinical results) of base cream and base cream using cytomimetic formulate are presented in Table 19.

The body of results obtained, as shown through in vitro and in vivo experiments, demonstrate the superiority of the aesthetic treatments through the cytomimetic formulas of the invention. Non-limiting examples are given below, describing the production, characteristics and use of the formulate of the invention.

Example 1

Preparation of Fermented Truffle Extract

1 Kg of *Tuber magnatum preciosa*, a white truffle collected from Alba, Italy, were washed first with water many times, then three times with 0.1 M sodium phosphate buffer at pH 6 and minced into small pieces. The truffle pieces were suspended with 0.1 M sodium phosphate buffer at pH 6 in the ratio 1/10 w/v and homogenized for 1 hour with an ultra Turrax blender.

The slurry was transferred into a 20 L fermenter and, after addition of 10 g of lyophilized *Saccharomices cerevisiae* inoculum, was fermented for 24 h at 30° C. with a flux of sterile air of 2 L/min, which automatically controlled the pH at 6. During fermentation its evident the partial clarification of the slurry. At the end of fermentation process the slurry was clarified by continous centrifugation on alfa Lavall centrifuge and the clear supernatant was lyophilised, obtaining 110 g of a pale yellow fine powder of fermented truffle extract.

Simple truffle extract was obtained by homogenizing washed truffle and maintaining under agitation of the slurry at 4° C. for 24 h, before clarification and lyophilization.

Fermented yeast extract was obtained by suspending 10 g of lyophilized *Saccharomices cerevisiae* in 10 L of 0.1 M sodium phosphate buffer at pH 6. The suspension was transferred in a 20 L fermenter, and fermented for 24 h at 30° C. with a flux of sterile air of 2 L/min, automatically controlling the pH at 6. At the end of fermentation process the suspension was clarified by continous centrifugation on Alfa Lavall centrifuge and the clear supernatant was lyophilised.

Example 2

Fermented Truffle Extract: In Vitro Keratinocytes and Fibroblast Scratch Assay, Using TLVM HaCaT, a spontaneously transformed non-tumorigenic human keratinocytes cell line was provided by Istituto Zooprofilattico, Brescia, Italy and the cells were cultured in Dulbecco's Modified Eagle Medium (DMEM), supplemented with 10% (v/v) heat inactivated Fetal Bovine Serum (FBS), penicillin 100 U/ml and streptomycin 100 μg/ml. DMEM, FBS, Pen-Strep PBS and Trypsin were provided by Gibco Invitrogen (Milan, Italy).

A human dermal fibroblasts cell line immortalized with hTERT (HDF cells, BJ-5ta, ATCC CRL-4001), was cultured in a 4:1 mixture of DMEM and Medium 199 supplemented with 0.01 mg/ml hygromycin B and 10% (v/v) FBS. All materials for HDF culture were purchased from ATCC (USA). The cells were grown on tissue culture plates (BD Falcon, Italy), using an incubator with a humidified atmosphere (95% air/5% $CO_2$ v/v) at 37° C.

Briefly 12-wells (pre-coated with collagen) were seeded with HaCat or HDFcells until complete confluence was reached. Scratch wounds were created mechanically with a sterile pipette tip (Ø=0.1 mm). Uniformly sized scratches were carefully obtained approximately 0.7±0.2 mm in width. Detached cells and debris were washed away with PBS solution before placing the multiwell in the stage incubator.

In both models, the effect of truffle extract, fermented truffle extract and fermented yeast on the rate of wound closure were tested by incubating the scratched monolayer with the following solution: truffle extract 1% w/v, fermented truffle extract 0.5 and 1% w/v and fermented yeast 1% w/v. The samples were prepared by dissolving the lyophilized powders directly in the medium. pH and osmolality (7.2-7.4 and 300 mosm) of the medium containing the treatments were verified to ensure physiological conditions.

The 'wound closure' phenomenon was monitored using a TLVM station, to observe the migration of cells to repair the wound. In the presence of different treatments, this allowed simultaneous observation of the repair of different cells and successive performance of qualitative and quantitative analyses of the experiment (D'Agostino et al., 2015, BMC cell biology, 16:19, hereby incorporated by reference).

The fermented truffle extract samples led to complete repair in shorter time compared with truffle extract, fermented yeast and control (Table 1).

Example 3

Effect of Fermented Truffle Extract on HSP 70 and HSP 90 Induction 20 mg of powder of fermented truffle extract or truffle extract or yeast lysate were resuspended in 1 ml of PBS (physiological conditions) in order to obtain a final concentration of 20 mg/ml.

2.5 millions of HEK-293t cells were treated with: 1, 2, 5 and 10 mg of fermented truffle extract in a final volume of 10 ml (DMEM medium). The cells were incubated for 18 hrs at 37° C. and then harvested. The cells were lysated in RIPA buffer (50 mM Tris pH 8, 1% nonidet p40 0.25% Sodium Deoxycholate and 1 mM EDTA) and equal amounts (calculated using the Bradford protein assay) of soluble fractions were loaded on SDS-PAGE (10% polyacrylamide). The gel was blotted on PVDF membrane and HSP 70/90 were detected using commercial antibodies. Anti-ß-actin was used as control. The signals corresponding to HSP 70 and HSP 90 were quantified using Image J software and the results obtained were plotted.

Analyzing the cells treated as described above, it was observed that HSP 70 and HSP 90 gradually increased their expression when cells where treated with increasing amounts of fermented truffle extract (mg of fermented truffle extract/ml of medium). The filters were quantified and the results obtained were blotted on a graph that clearly indicates a peak of HSP 70/90 expression levels at 1 mg/ml (Table 2)

Data indicate that HEK-293t cells treated with fermented truffle extract show with a progressive increase, concentration dependent, of HSP 70 and HSP 90 level of expression, this effect is in minor amount present with fermented yeast and absent with non fermented truffle extract.

Example 4

Antioxidant In Vitro Activity of Fermented Truffle Extract Using T-BARS (Thiobarbituric Acid Reactive Substances) Assay Generation of reactive aldehydes were assessed by measuring thiobarbituric acid-reactive substances (TBARS), as described previously by Stiuso et al., (Stiuso P., et al., 2014, Oxidative Medicine and Cellular Longevity, hereby incorporated by reference). The effect of fermented truffle extract on HaCaT cells ($2.0 \times 10^5$) was tested in three different experimental setups: (1) cells were pre-treated for 30 minutes with 50 μM $H_2O_2$ or with exposure to a UVA radiation ($\lambda_{max}$ 365 nm), and then incubated with fermented truffle extract (0.32% w/v) for 24 h, to test the protection effect on post-stress process; (2-3) fermented truffle extract was applied simultaneously with 50 μM $H_2O_2$ or with exposure to a UVA radiation ($\lambda_{max}$ 365 nm), to test its antioxidant activity.

The protein concentrations were determined using the Bio-Rad protein assay reagent (Bio-Rad Laboratories, Milan Italy). Lipid peroxidation was evaluated using an analytical quantitative methodology. It relies upon the formation of a colored adduct produced by the steochiometric reaction of aldehydes (malondialdehydes MDA) with thiobarbituric acid (TBA).

TBARs assay were performed on aliquots of membranes extracted (10 μl) added to 2 ml of TBA-TCA (TCA 15% w/v, TBA 0.3% w/v In HCl 0.12 N) solution at 100° C. for 30 min. The chromogen was quantified by spectrophotometric reading at a wavelength of 532 nm and the amount of TBARs were expressed as a percentage of lipid peroxidation and then normalized respect to control. Data reported in Table 3 shows that fermented truffle extract is effective in all oxidative stress conditions.

Example 5

Production of HA of Different Mw

The strategy used to obtain HA of different Mw is based on an heterogeneous acid hydrolysis of 1800 KDa HA according to Toommeras et al., (Melander C. and Tommeraas K., 2010, Carbohydrate Polymers 82, 874-879, hereby incorporated by reference). In particular, HA powder (1800 kDa) hydrolysis in ethanol (EtOH) (93% v/v) was carried out using a HCl-EtOH vs. HA ratio 10/1 v/w. The slurry was pre-warmed at 65° C. in a thermostatic bath, then a few drops of HCl 37% v/v were added under vigorous stirring, in order to have a final concentration of 0.4M HCl. The hydrolysis was carried out for 60 and 100 min to obtain HA 800 and 200 KDa respectively. Each sample was then cooled in an ice-bath and neutralized with an equimolar quantity of $NH_3$ 25%. Samples were washed with ethanolic solution (93% v/v), recovered using a Buchner funnel under vacuum, lyophilized and then stored at −20° C. until characterization was obtained.

HA fragments were characterized by SEC-TDA (Size Exclusion Chromatography—Triple Detector Array) equipment by Viscotek (Lab Service Analytica, Italy). A detailed description of the system and its analytical conditions are reported by La Gatta et al. (La Gatta et al., J Biomed Mater Res Part B: Appl Biomater, 104B, 9-18, hereby incorporated by reference).

Samples' molecular weight (Mw, Mn, Mw/Mn) and molecular size (hydrodynamic radius—Rh) are reported in Table 4. The poly dispersity index ranged from 1.4 to 1.7, which was comparable to the one calculated for the HA substrate, confirming an efficient and a simple approach for degrading HA without further complex purification steps. The decrease of intrinsic viscosity and hydrodynamic radius were in accordance with the reduction of chain lengths.

In order to confirm if HA, degraded by heterogeneous hydrolysis, maintained its structural integrity, the hydrolysed HA fragments were analyzed by $^1$H-NMR spectroscopy. As expected, the $^1$H-NMR spectra showed the presence of peaks corresponding to acetamide protons at 1.9 ppm, 2', 3', 4', 5', and 6'-protons of HA disaccharide unit at 3.2-4.0 ppm, as well as anomeric 1'-protons at 4.4 ppm. No indication of suspected by-products such as de-N-acetylation or ethanolysis at the reducing-end were observed.

Endotoxin amount determination—For endotoxin content determination, HA powders were dissolved in pyrogen free water. The amount of pyrogens (bacterial endotoxins) in the solution were measured by using Limulus Amebocyte Lysate (LAL) testing (chromogenic kinetic method) according to European Pharmacopoeia 01/2005:20614. Specifically, ENDOSAFE®-PTS cartridge US License N.1197 by Charles River Endosafe were used. All operations were performed under conditions avoiding endotoxin contamination. Results were reported as endotoxin units (EU/mg) of HA powder. The low endotoxin content, crucial in pharma grade requirements, is of key importance to better highlight the HA fragment function itself. The endotoxins amount for all hyaluronan powders produced, resulted in less than 0.05 EU/mg. This data proved that LPS and/or endotoxin are below a guard level and therefore cellular phenomenon should be driven by HAs rather than impurities.

Example 6

HAs: In Vitro Keratinocytes and Fibroblasts Scratch Assay, Using TLVM

HaCaT and HDF cell line and their growth conditions are described herein above in Example 2. In both models, the effect of HA gels on the rate of wound closure was tested by incubating the scratched monolayer with the following solutions: HA1800 KDa, HA800 KDa, HA200 KDa, HA1800

KDa+HA800 KDa (50% w/w each), and HA1800 KDa+HA800 KDa+HA200 KDa (33.3% w/w each) at final concentration of 1% w/w in the incubation medium. The samples were prepared by dissolving the lyophilized powder directly in the medium. pH and osmolarity (7.2-7.4 and 300 mosm) of the medium containing the treatments were verified to ensure physiological conditions.

The 'wound closure' phenomenon was monitored using a TLVM station to observe the migration of cells to repair the wound. In the presence of different treatments, this allowed simultaneous observation of the repair of different wells and successive performance of qualitative and quantitative analyses of the experiment (D'Agostino et al., 2015 BMC cell biology, 16:19).

The highest Mw HA samples led to complete repair in shorter time; however, all the HA fragments tested enhanced the scratch repair rate compared to the control (Table 5).

Mixtures formed by equivalent amounts in weight of HA1800+HA800 KDa and HA1800+HA800+HA200 KDa are characterized by a significant reduction in the repair time with respect to HA separately (Table 5).

Example 7

HAs: Gene Expression Analysis in Stressed Cells

For gene expression analyses in stressful conditions, human keratinocytes and fibroblasts were grown in different cell cultures. $3.75 \times 10^4$ cells/cm$^2$ were seeded in a standard 24-well culture plate. To reproduce skin inflammation in vitro, the mechanical injury induced to the cultures was very extensive. With a sterile tip, parallel scratches were inflicted upon the monolayers, estimating damage to be at least 40% of the cells.

After addition of HAs and incubation for 16 h the cells were directly lysed with TRIzol® (Invitrogen, Milan, Italy). Total RNA was extracted from HA (Mw=1800, 800 and 200 KDa) treated keratinocytes or fibroblasts. Following precipitation with isopropyl alcohol and washing with 75% ethanol, the RNA pellets were resuspended in nuclease-free water. The concentration of the extracted RNA was determined through a Nanodrop spectrophotometer (Celbio, Milan, Italy) and 1 µg of DNase-digested total RNA was retro-transcripted in the cDNA using Reverse Transcription System Kit (Promega, Milan).

Quantitative real time PCR was obtained by iQ™ SYBR® Green Supermix (Bio-Rad Laboratories Srl) in order to analyze the gene expression of some HA key receptors such as CD44 and RHAMM, TLR4 and alert inflammation biomarkers such as TGF-β, TNFα, IL-6. The primer sequences (Table 6) were designed by Beacon Designer™ software. The final melting curve was performed from 55-95° C.

Samples were run in triplicate, and the expression of specific mRNA relative to the control was determined after normalization with respect to HPRT housekeeping gene (internal control). The fold-change of mRNA expression of the genes under evaluation was calculated by using the 2-ΔΔCt comparative threshold method (ΔΔCt=difference of ΔCt between treated cells and non-treated cells used as controls). The results were expressed as normalized fold expression, calculated by the ratio of crossing points of amplification curves of several genes and internal standard, by using the Bio-Rad iQ™5 software (Bio-Rad Laboratories Srl). Gene expression data analyses for the main HA receptors are reported in Table 7. CD44 was to be over expressed for all HA evaluated. All HA samples increased RHAMM expression, however results were significantly higher for 200 KDa.

Inflammation biomarkers (TGFβ-1, TNF-α and IL-6) involved in epithelial cell migration were evaluated by quantitative RT-PCR. Specifically, TGFβ-1 was up-regulated for all HA fragments investigated. HA ranging from 800 to 200 KDa, showed a significant increase in TGFβ-1 with respect to HA1800 KDa.

In this case the increase prompted a "positive" activation toward the repair. Cell repair activation mechanism, implicate also IL-6 that is regulated by HA/receptor interaction. Results showed that both TNF-α and IL-6 present similar trend during re-epithelisation process. In particular the expression levels increased with the HA molecular size decreasing.

Example 8

HAs: Antioxidant In Vitro Activity Using T-BARS (Thiobarbituric Acid Reactive Substances) Assay The experiment was conducted as reported in the Example 4. The effect of HAs 1800+800+200 KDa mixture (33.3% w/w each) at final concentration of 0.5% w/v in the incubation medium, on HaCaT cells ($2.0 \times 10^5$) was tested in three different experimental setups: (1) cells were pre-treated for 30 min with 50 µM $H_2O_2$ or with exposure to a UVA radiation (λmax 365 nm) and then incubated with HAs mixture (0.5% w/v) for 24 h, to test the protection effect on post-stress process; (2-3) HAs mixture were applied simultaneously with 50 µM $H_2O_2$ or with exposure to UVA radiation (λmax 365 nm) to test antioxidant activity.

Data reported in Table 8 show that HAs 1800+800+200 KDa mixture (33.3% w/w each) is effective in the oxidative stress conditions.

Example 9

Preparation of Olive Leaf Extract in Thermal Water and Characterization of Actives 10 Kg of fresh Olive leaves, collected from centuries-old olive trees of Puglia, Italy, were washed first with water a plurality of times, then suspended in 40 L of thermal water from the Thurio spring at the Spezzano Thermal Baths, Italy. Then they were homogenized for 1 h with an ultra Turrax blender. At the end of extraction process (24 h, 4° C., pH 5.5-6.5) the slurry was clarified by continous centrifugation on Alfa Lavall centrifuge and the clear pale green supernatant was directly used in the cosmetic formulate.

To characterize the extract the solution was lyophilised. Quantitative chemical characterization of actives present in the extract indicates a solid residue of 50 g/L of extract containing per g of powder 50 mg of oleuropein, 6 mg of minor olive polyphenol and 1 mg of flavonoids.

Example 10

Olive Leaf Extract in Thermal Water: In Vitro Keratinocytes and Fibroblasts Scratch Assay, Using TLVM HaCaT and HDF cell line and their growth conditions are described hereinabove in Example 2. In both models, the effect of Olive leaf extract in thermal water on the rate of wound closure was tested by incubating the scratched monolayer with a final concentration of 20% v/v in the cell growth medium.

The 'wound closure' phenomenon was monitored using TLVM station, to observe the migration of cells to repair the wound (D'Agostino et al., 2015 BMC cell biology, 16:19, hereby incorporated by reference).

Results (Table 9) indicate a significant synergism of action between the thermal water and the active present in the olive leaf extract. It was almost half the time of closure of the wound.

Example 11

Olive Leaf Extract in Thermal Water: Antioxidant In Vitro Activity Using T-BARS (Thiobarbituric Acid Reactive Substances) Assay The experiment was conducted as reported in Example 4. The effect of Olive leaf extract in thermal water and in water at final concentration of 10% v/v in the incubation medium, on HaCaT cells ($2.0\times10^5$) was tested in three different experimental setups: (1) cells were pre-treated for 30 min with 50 µM $H_2O_2$ or with exposure to a UVA radiation ($\lambda$max 365 nm) and then incubated with Olive leaf extract in thermal water (10% v/v) for 24 h, to test the protection effect post-stress process; (2-3) Olive leaf extract in thermal water was applied simultaneously with 50 µM $H2O2$ or with exposure to UVA radiation ($\lambda$max 365 nm) to test antioxidant activity.

Data reported in Table 10 show that Olive leaf extract in thermal water is effective in but the oxidative stress conditions.

Example 12

Production of Fermented Grapes of Falernum

50 Kg of fresh grapes collected from Falciano del Massico, (Italy) vineyards (the same used by ancient Romans to produce the most expensive and famous Faustian Falernian wine) were washed twofold with water, and after premixing were homogenized for 1 h with an ultra Turrax blender. At the end of fermentation process (48 h, 10° C., pH 5) the slurry was clarified by under pressure filtration and pasteurised.

25 L of a stable solution of a brilliant ruby was obtained, rich in polyphenols with antioxidant activity and a complex mixture of carbohydrate and peptide compounds, which confer a strong biorevitalizing action.

Example 13

Fermented Grapes of Falernum: In Vitro Keratinocytes and Fibroblasts Scratch Assay, Using TLVM HaCaT and HDF cell line and their growth conditions are described herein above in Example 2. In both models, the effect of the fermented grapes of Falernum on the rate of wound closure was tested by incubating the scratched monolayer with a final concentration of 10% and 20% v/v in the cell growth medium.

The 'wound closure' phenomenon was monitored using TLVM station, to observe the migration of cells to repair the wound (D'Agostino et al., 2015 BMC cell biology, 16:19, hereby incorporated by reference). Results (Table 11) indicate a reduction of the wound closure time in presence of fermented grapes of Falernum to about half of the control for both the cellular systems used.

Example 14

Fermented Grapes of Falernum: Antioxidant In Vitro Activity Using T-BARS (Thiobarbituric Acid Reactive Substances) Assay The experiment was conducted as reported in Example 4. The effect of fermented grapes of Falernum at final concentration of 10% v/v in the incubation medium, on HaCaT cells ($2.0\times10^5$) was tested in three different experimental setups: 1) cells were pre-treated for 30 min with 50 µM $H_2O_2$ or with exposure to a UVA radiation ($\lambda$max 365 nm) and then incubated with fermented grapes of Falernum (10% v/v) for 24 h, to test the protection effect post-stress process; (2-3) fermented grapes of Falernum were applied simultaneously with 50 µM $H_2O_2$ or with exposure to UVA radiation ($\lambda$max 365 nm) to test antioxidant activity. Data reported in Table 12 show that fermented grapes of Falernum is effective in all the oxidative stress conditions.

Example 15

Cytomimetic Formula Preparation

1 L of fermented grapes of Falernum, prepared as reported in Example 10, were mixed with 0.5 L of Olive leaf extract in thermal water, prepared as reported in Example 8. This solution was diluted with 3 L of deionized water and under agitation 0.3% EDTA, 0.4% sodium benzoate, 12.5 g of 1800 KDa HA, 12.5 g of 800 KDa HA and 12.5 g of 200 KDa and 5 g of fermented truffle extract prepared as reported in Example 1 were added.

The pH was corrected at 6.5 with 3% NaOH solution and the solution was diluted with deionized water up to 5 L. A clear ruby solution was obtained.

The resulting composition of the cytomimetic formula is: fermented truffle extract powder 0.1% (w/v); fermented graped of Falernum 20% v/v; Olive leaf extract in thermal water 10% v/v; and HA 1880, 800, 200 KDa each 0.25% w/v.

Example 16

Synergistic Action of Actives of the Cytomimetic Formulas: In Vitro Scratch Wound-Healing Assay Using TLVM HaCaT and HDF cell line and their growth conditions are described hereinabove in Example 2. In both models, the effect of the cytomimetic formula on the rate of wound closure was tested by incubating the scratched monolayer with a final concentration of 1% and 2% v/v in the cell growth medium.

The 'wound closure' phenomenon was monitored using a TLVM station to observe the migration of cells to repair the wound (D'Agostino et al., 2015 BMC cell biology, 16:19). Results (Table 9) indicate a reduction of the wound closure time in presence of the cytomimetic formula to about ¼ of the control for both the cellular systems used. The data in Table 13 demonstrate a potent synergistic effect of the actives present in the cytomimetic formula, which in this experiment are present up to three orders of magnitude in respect to that reported in Examples 2, 6, 10 and 13 for the single actives.

Example 17

Synergistic Action of Actives of the Cytomimetic Formula: Antioxidant In Vitro Activity of the Cytomimetic Formula Using T-BARS (Thiobarbituric Acid Reactive Substances) Assay Generation of reactive aldehydes was assessed by measuring thiobarbituric acid-reactive substances (TBARS), as described previously by Stiuso et al., (Stiuso P., et al., 2014, Oxidative Medicine and Cellular Longevity). The effect of the cytomimetic formula on HaCaT cells ($2.0 \times 10^5$) were tested in three different experimental setups: 1) cells were pre-treated for 30 min with 50 µM $H_2O_2$ or with exposure to a UVA radiation ($\lambda$max 365 nm) and then incubated with cytomimetic formula (0.1 or 0.5% v/v) for 24 h, to test the protection effect post-stress process; (2-3) cytomimetic formula (0.32% w/w) was applied simultaneously with 50 µM $H_2O_2$ or with exposure to UVA radiation ($\lambda$max 365 nm) to test antioxidant activity.

The protein concentrations were determined using the Bio-Rad protein assay reagent (Bio-Rad Laboratories, Milan Italy). Lipid peroxidation was evaluated using an analytical quantitative methodology. It relies upon the formation of a colored adduct produced by the stechiometric reaction of aldehydes (malondialdehydes MDA) with thiobarbituric acid (TBA).

TBARs assay were performed on aliquots of membranes extracted (10 µl) and added to 2 ml of TBA-TCA (TCA 15% w/v, TBA 0.3% w/v in HCl 0.12 N) solution at 100° C. for 30 min. The chromogen was quantified by spectrophotometric reading at a wavelength of 532 nm and the amount of TBARs were expressed as a percentage of lipid peroxidation and then normalized with respect to control.

Data reported in Table 14 show whether oxidative stress occurred before or with the addition of the cytomimetic formula was effective.

Example 18

Synergistic Action of Cytomimetic Formulate: Effect on HSP 70 and HSP 90 Induction 2.5 millions of HEK-293t cells were treated with a cytomimetic formulation at 0.1 and 0.5% v/v in a final volume of 10 ml (DMEM medium). The cells were incubated for 18 h at 37° C. and then harvested. The cells were lysated in RIPA buffer (50 mM Tris pH 8, 1% nonidet p40 0.25% Sodium Deoxycholate and 1 mM EDTA) and equal amounts (calculated using the Bradford protein assay) of soluble fractions were loaded on SDS-PAGE (10% polyacrylamide). The gel was blotted on PVDF membrane and HSP 70/90 were detected using commercial antibodies. Anti-ß-actin was used as control. The signals corresponding to HSP 70 and HSP 90 were quantified using Image J software and the results obtained were plotted.

Analyzing the cells treated as described above, it was observed that HSP 70 and HSP 90 gradually increased their expression when cells where treated with increasing amounts of the cytomimetic formulation.

Data from Table 15 indicate the potent synergistic effect of actives present in the cytomimetic formulation, that in this experiment are present at an average two orders of magnitude with respect than that reported in Example 3 for the fermented truffle extract alone.

Example 19

Cytomimetic Formulate: Gene Expression Analysis in Stressed Cells

The gene expression analyses of the cytomimetic formulation in stressful conditions was performed at 0.1 and 0.5% v/v as described hereinabove in Example 7. Gene expression data analyses are reported in Table 16. CD44, RHAMM, TGFβ-1, TNF-α and IL-6 are all up-regulated increasing Cytomimetic formulate concentration, only TLR-4 activity, correlated to inflammatory process, is significantly down-regulated.

Example 20

Base Cosmetic Formulations

An example of composition used as base to test the cytomimetic formulation described in Example 12 as reported in Table 17. Below is the modus operandi of this cosmetic product. In the main vessel, water is heated to 60° C. Ingredients A2 through A6 are added with medium agitation. Then mixed until uniform. In the secondary vessel phase B is prepared: ingredients B1-21 are added and temperature increased to 60° C. Each ingredient is blended in before adding the next one. The ingredients are mixed until homogenous. Phase B (oil phase) is added onto water phase (phase A) and homogenized using low speed. Phase C (preservatives) is added and cooled down to 25° C. Then the fragrance is added.

Example 21

Cosmetic Treatment

An example of composition using Cytomimetic formulation described in Example 12 is reported in Table 18. Below is the modus operandi of this cosmetic product. In the main vessel water is heated to 60° C. Ingredients A1 through A6 are added with medium agitation, then mixed until uniform. Into the secondary vessel phase B is prepared: ingredients B1-B21 are added and temperature increased to 60° C. Each ingredient is blended in before adding the next one and then mixed until homogenous. Phase B (oil phase) is added onto the water phase (phase A) and homogenized using low speed. Phase C (cytomimetic formulation) is added, followed by phase D (preservatives). It is then cooled down to 25° C. and then the fragrance added.

Example 22

Clinical Testing Methodology

The testing application of the base composition and base composition using a cytomimetic formulation is made by subjects morning and night, through a gentle massage, so as to have full-absorption of the product. The measurements will be done in the right and left zygomatic arch (1 cm. extension of the external angle), on the cleansed skin, having not used make-up in the previous 24 hours. This is done after acclimatization of the subjects for at least 10 minutes in constant temperature/humidity conditions. Each of the two products will be evaluated against baseline initial measurements.

The efficacy will be appreciated through instrumental, non-invasiveness methods: moisture of corneum layer (Corneometry), sebumetry, elasticity and firmness, SELS (Surface Evaluation of Living Skin) parameters: roughness, smoothness, the scaliness degree, wrinkles). Successive measurements will be done, as follows: for moisture (triplicate in each point: left/right), for sebumetry, elasticity, firmness and profilometry an unique measurement right/left, as follows: for the hydration (Corneometer MPA 580, Courage+Khazaka electronic GmbH), sebumetry (Sebumeter SM 815, Courage Khazaka electronic GmbH), elasticity (cutometer MPA 580, Courage+Khazaka electronic GmbH), profilometry (Visioscan VC80, Courage+Khazaka electronic GmbH).

Skin Hydration is determined instrumentally, through Corneometry. Measurement principle: measuring the capacitance. Water increases the capacitance of the capacitor as compared with a vacuum capacitor ($C=\varepsilon S/d$). The water dielectric constant $\varepsilon$ is 81, as compared with other substances <7 and the vacuum dielectric constant is 1. The changes in capacitance due to variations in the dielectric constant give the level of hydration. The corneometer measures the water content in the surface epidermal layer up to a depth of 0.1 mm.

The sebumetry is determined instrumentally, with the help of a sebumeter. The measurement is based on the absorbance of a plastic film impregnated with sebum is determined through photometry, the film becoming transparent in the presence of the lipids. The sebum values that can me measured are between 50-300 $\mu g/cm^2$. Values exceeding 300 $\mu g/cm^2$ indicate excess sebum supersaturation and may be subject to measurement errors, while values below 50 $\mu g/cm^2$ show that there is no linearity between the values and the sebum content.

Measurements for skin elasticity are made with a Cutometer. The measurement principle is based on suction and elongation. The device generates a negative pressure between 20 and 500 mbar which "sucks up" a defined skin area it is applied to. In order to measure the mechanical characteristics of the epidermis 2 mm diameter probes are necessary while for the dermis and hypodermis—10 mm diameter probes. When measuring the elasticity parameters it is important to set the suction pressure according to the characteristics of the skin (e.g.: the skin around the eyes is thinner—the suction pressure is lower). The measurements will be done in Module 1, with a 2 mm probe, negative constant pressure 350 mbars, 2 seconds time of the sucction and relaxation. The number of repetitions will be 10, in order to evaluate the skin firmness and the tiredness resistance.

The testing method is called SELS (Surface Evaluation of the Living Skin) and it is based on the graphic illustration of the skin surface in special lighting conditions. This image is processed electronically taking into account four clinical parameters which correspond to the physiological conditions of the skin surface both from the quantitative and from the qualitative point of view and which derive from the roughness conventional parameters.

TABLE 1

In vitro scratch wound-healing assay using TLVM and as cellular model HaCaT chondrocytes and HDF fibroblasts. Cells were stimulated with truffle extract and two different concentrations of fermented truffle extract.

| | Cellular model | | | | | |
|---|---|---|---|---|---|---|
| | HaCaT | | | HDF | | |
| | % of wound surface repaired | | | | | |
| | 50 | 80 | 100 | 50 | 80 | 100 |
| Sample | Repair time (h) | | | | | |
| Control | 22 | 33 | 56 | 21 | 40 | 63 |
| Truffle extract 0.1% w/v* | 18 | 25 | 40 | 20 | 26 | 42 |
| Fermented truffle extract 0.5% w/v** | 10 | 15 | 30 | 12 | 16 | 32 |
| Fermented truffle extract 1% w/v** | 8 | 11 | 18 | 8 | 12 | 20 |
| Fermented yeast 0.1% w/v*** | 16 | 21 | 36 | 18 | 23 | 38 |

*Extracted as described in Example 1
**Fermented truffle extract with *Saccharomyces cerevisiae* prepared and described in Example 1
***Fermented *Saccharomyces cerevisiae* prepared as described in Example 1

TABLE 2

Effect of fermented/non-fermented truffle extract and of fermented yeast on HSP 70 and HSP 90 induction

| | Concentration (% w/v) in the growth medium | | | | |
|---|---|---|---|---|---|
| Samples | 0.0 | 01 | 02 | 05 | 10 |
| | HSP 70 expression (respect to the control = 100) | | | | |
| Truffle extract* | 100 | 98 | 95 | 97 | 101 |
| Fermented truffle extract** | 100 | 105 | 130 | 138 | 180 |
| Fermented yeast*** | 100 | 101 | 105 | 110 | 125 |
| | HSP 90 expression (respect to the control = 100) | | | | |
| Truffle extract* | 100 | 96 | 97 | 100 | 102 |
| Fermented truffle extract** | 100 | 100 | 135 | 141 | 200 |
| Fermented yeast*** | 100 | 98 | 108 | 115 | 125 |

*Extracted as described in Example 1
**Fermented truffle extract with *Saccharomyces cerevisiae* prepared as described in Example 1
***Fermented *Saccharomyces cerevisiae* prepared as described in Example 1

TABLE 3

Antioxidant in vitro activity of fermented and non-fermented truffle extract using T-BARS (thiobarbituric acid reactive substances) assay (see Example 3).

| Sample (w/v in DMEM) | Protection during stress treatment* | Protection after stress treatment** | HaCaT Lipid peroxidation % respect the control | HDF Lipid peroxidation % respect the control |
|---|---|---|---|---|
| Control | | | 100 | 100 |
| No extract added | UV-A | | 460 | 438 |
| Fermented truffle extract 0.5% | UV-A | | 101 | 108 |
| Truffle extract 0.5% | UV-A | | 218 | 190 |
| No extract added | $H_2O_2$ | | 525 | 538 |
| Fermented truffle extract 0.5% | $H_2O_2$ | | 112 | 120 |
| Truffle extract 0.5% | $H_2O_2$ | | 198 | 205 |
| Fermented truffle extract 0.5% | | UV-A | 111 | 121 |
| Truffle extract 0.5% | | UV-A | 230 | 211 |

TABLE 3-continued

Antioxidant in vitro activity of fermented and non-fermented truffle extract using T-BARS (thiobarbituric acid reactive substances) assay (see Example 3).

| Sample (w/v in DMEM) | Protection during stress treatment* | Protection after stress treatment** | HaCaT Lipid peroxidation % respect the control | HDF |
|---|---|---|---|---|
| Fermented truffle extract 0.5% | $H_2O_2$ | | 109 | 119 |
| Truffle extract 0.5% | $H_2O_2$ | | 233 | 214 |

*Effect on lipid peroxidation of 0.5% w/v fermented truffle extract or non-fermented truffle extract present during stress conditions.
**Effect on lipid peroxidation of 0.5% w/v fermented truffle extract or non-fermented truffle extract applied after stress conditions.

TABLE 4

The table represented the extrapolated data of Viscotek analysis: molecular weight (Mw), poly dispersion index Mw/Mn, intrinsic viscosity (IV) and hydrodynamic radius.

| Sample (KDa) | Mw (KDa) | Mw/Mn | IV (dl/g) | Rh (nm) |
|---|---|---|---|---|
| HHA 1800 | 1835 ± 7 | 1.65 ± 0.12 | 24.91 ± 0.32 | 87.06 ± 0.43 |
| HHA 1400 | 1398 ± 9 | 1.50 ± 0.14 | 22.11 ± 0.91 | 67.09 ± 0.10 |
| LHA 800 | 788 ± 5 | 1.62 ± 0.11 | 17.01 ± 0.23 | 48.11 ± 0.32 |
| LHA 200 | 198 ± 3 | 1.42 ± 0.22 | 3.78 ± 0.44 | 20.15 ± 0.60 |
| LHA 100 | 97 ± 5 | 1.52 ± 0.24 | 2.88 ± 0.33 | 15.19 ± 0.55 |
| LHA 50 | 51 ± 5 | 1.66 ± 0.20 | 1.71 ± 0.31 | 11.71 ± 0.33 |

TABLE 5

In vitro scratch wound-healing assay using TLVM and as cellular model HaCaT chondrocytes and HDF fibroblast. Cells were stimulated with HA 1800, 800, 200 KDa and their mixture (1% w/w respect to growth medium).

| | Cellular model | | | | | |
|---|---|---|---|---|---|---|
| | HaCaT | | | HDF | | |
| | % of wound surface repaired | | | | | |
| | 50 | 80 | 100 | 50 | 80 | 100 |
| Sample (KDa) | Repair time (h) | | | | | |
| Control | 20 | 31 | 55 | 22 | 38 | 60 |
| HA1800 | 4 | 12 | 21 | 6 | 16 | 28 |
| HA800 | 10 | 15 | 35 | 12 | 18 | 39 |
| HA200 | 12 | 20 | 40 | 16 | 26 | 45 |
| HA1800 + HA800 | 3 | 10 | 18 | 5 | 14 | 20 |
| HA1800 + HA800 + HA200 | 3 | 8 | 15 | 4 | 10 | 17 |

TABLE 6

Oligonucleotide sequences relative to biomarkers used. Forward primers are, top to bottom respectively, SEQ ID NOS: 1-6. Reverse primers are, top to bottom respectively, SEQ ID NOS: 7-12.

| Gene | Forward primer | Reverse primer | Primer Cycles |
|---|---|---|---|
| Transforming growth factor, beta 1 (TGFβ-1) | 5'TgCggCAgCTgTACATTgA3' | 5'TggTTgTACAgggCCAggA3' | 95° C. 10 s, 55° C. 30 s, 72° C. 3 min, 40 cycles |
| Tumor necrosis factor alpha (TNFα) | 5'CgAgTgACAAgCCTgTAg3' | 5'ggTgTgggTgAggAgCACAT3' | 94° C. 1 min, 55° C. 2 min, 72° C. 3 min, 40 cycles |
| Interleukin (IL-6) | 5'gCCgCCTTTAACTggAgCAA'3 | 5'TTCCAggCATCTgCgATgAg3' | 95° C. 10 s, 55° C. 30s, 72° C. 3 min, 40 cycles |
| Cluster of differentiation 44 (CD44) | 5' gCgCCACCACAgCCAACTATg '3 | 5'TggATGCCgTCTATgTCgTC TTTA3' | 94° C. 1 min, 60° C. for 2 min, 72° C. 3 min, 40 cycles |
| Toll-like receptors 4 (TLR4) | 5'TCCCAggAATTggTgATAAAgT AgA'3 | 5'CTggCATgACgCgAACAAT A'3 | 95° C. 10 s, 60° C. 30 s, 72° C. 3 min, 40 cycles |
| Receptor for Hyaluronan Mediated Motility (RHAMM) | 5'gATAATCCgCATTCAgTTgTC-3' | 5'TAACATCATAAGCACCTG GAG-3' | 95° C. 10 s, 60° C. 30 s, 72° C. 3 min, 40 cycles |

TABLE 7

Gene expression induced by HA of different Mw.

| | Cellular model | | | | | |
|---|---|---|---|---|---|---|
| | HaCaT | | | HDF | | |
| | Normalized fold expression | | | | | |
| | HA Mw (KDa) | | | | | |
| | 1800 | 800 | 200 | 1800 | 800 | 200 |
| CD44 | 5.1 | 4.8 | 4.0 | 6.8 | 5.3 | 3.1 |
| RHAMM | 4.8 | 2.3 | 12.2 | 5.7 | 2.9 | 14.0 |
| TLR-4 | 0.8 | 0.6 | 0.5 | 1.1 | 0.9 | 1.2 |
| TGF-β1 | 4.6 | 15.2 | 15.0 | 5.8 | 14.6 | 18.3 |
| TNFα | 3.1 | 6.2 | 4.1 | 2.9 | 7.5 | 5.6 |
| IL-6 | 1.7 | 3.8 | 3.4 | 2.5 | 4.5 | 4.6 |

TABLE 8

Antioxidant in vitro activity of HA1800 + HA800 + HA200 using T-BARS (thiobarbituric acid reactive substances) assay.

| Sample (v/v in DMEM) | Protection during stress treatment* | Protection after stress treatment** | HaCaT Lipid peroxidation % respect the control | HDF Lipid peroxidation % respect the control |
|---|---|---|---|---|
| Control | | | 100 | 100 |
| No additions reference | UV-A | | 450 | 460 |
| HA1800 + HA800 + HA200 | UV-A | | 132 | 139 |
| No additions reference | $H_2O_2$ | | 533 | 540 |
| HA1800 + HA800 + HA200 | $H_2O_2$ | | 118 | 122 |
| HA1800 + HA800 + HA200 | | UV-A | 121 | 118 |
| HA1800 + HA800 + HA200 | | $H_2O_2$ | 131 | 127 |

*Effect on lipid peroxidation of 0.5% w/v HA1800 + HA800 + HA200 present during stress conditions.
**Effect on lipid peroxidation of 0.5% w/v HA1800 + HA800 + HA200 applied after stress conditions.

TABLE 9

In vitro scratch wound-healing assay using TLVM and as cellular model HaCaT chondrocytes and HDF fibroblasts. Cells were stimulated with Olive leaf extract in thermal water prepared as described in Example 10.

| | Cellular model | | | | | |
|---|---|---|---|---|---|---|
| | HaCaT | | | HDF | | |
| | % of wound surface repaired | | | | | |
| | 50 | 80 | 100 | 50 | 80 | 100 |
| Sample | Repair time (h) | | | | | |
| Control | 23 | 30 | 51 | 23 | 38 | 60 |
| Olive leaf extract in thermal water 10% v/v* | 12 | 16 | 30 | 12 | 15 | 31 |
| Olive leaf extract in water 10% v/v* | 16 | 20 | 39 | 18 | 21 | 38 |
| Thermal water | 20 | 25 | 45 | 21 | 30 | 50 |

*% respect to growth medium

TABLE 10

Antioxidant in vitro activity of Olive leaf extract in thermal water using T-BARS (thiobarbituric acid reactive substances) assay.

| Sample (v/v in DMEM) | Protection during stress treatment* | Protection after stress treatment° | HaCaT Lipid peroxidation % respect the control | HDF Lipid peroxidation % respect the control |
|---|---|---|---|---|
| Control | | | 100 | 100 |
| No extract added | UV-A | | 435 | 440 |
| Olive leaf extract in thermal water 10% v/v* | UV-A | | 138 | 144 |
| No extract added | $H_2O_2$ | | 540 | 530 |
| Olive leaf extract in thermal water 10% v/v* | $H_2O_2$ | | 129 | 131 |
| Olive leaf extract in thermal water 10% v/v* | | UV-A | 133 | 142 |
| Olive leaf extract in thermal water 10% v/v* | | $H_2O_2$ | 123 | 131 |

*Effect on lipid peroxidation of 10% v/v Olive leaf extract in thermal water present during stress conditions.
**Effect on lipid peroxidation of 10% v/v Olive leaf extract in thermal water applied after stress conditions.

TABLE 11

In vitro scratch wound-healing assay using TLVM and as cellular model HaCaT chondrocytes and HDF fibroblasts. Cells were stimulated with fermented Falernum grapes prepared as described in Example 13.

| | Cellular model | | | | | |
|---|---|---|---|---|---|---|
| | HaCaT | | | HDF | | |
| | % of wound surface repaired | | | | | |
| | 50 | 80 | 100 | 50 | 80 | 100 |
| Sample | Repair time (h) | | | | | |
| Control | 22 | 33 | 50 | 22 | 36 | 58 |
| Fermented Falernum grapes 10% v/v* | 18 | 24 | 40 | 19 | 23 | 45 |
| Fermented Falernum grapes 20% v/v* | 13 | 19 | 29 | 14 | 19 | 28 |

*% respect to growth medium

TABLE 12

Antioxidant in vitro activity of fermented Falernum grapes 10% v/v* using T-BARS (thiobarbituric acid reactive substances) assay.

| Sample (v/v in DMEM) | Protection during stress treatment* | Protection after stress treatment° | HaCaT Lipid peroxidation % respect the control | HDF Lipid peroxidation % respect the control |
|---|---|---|---|---|
| Control | | | 100 | 100 |
| No fermentate added | | | 453 | 455 |
| Fermented Falernum grapes 10% v/v* | UV-A | | 131 | 135 |
| No fermentate added | | | 545 | 560 |
| Fermented Falernum grapes 10% v/v* | $H_2O_2$ | | 133 | 145 |
| Fermented Falernum grapes 10% v/v* | | UV-A | 124 | 131 |
| Fermented Falernum grapes 10% v/v* | | $H_2O_2$ | 127 | 135 |

*Effect on lipid peroxidation of 10% v/v Fermented Falernum grapes present during stress conditions.
**Effect on lipid peroxidation of 10% v/v Fermented Falernum grapes 10% v/v applied after stress conditions.

TABLE 13

In vitro scratch wound-healing assay using TLVM and as cellular model HaCaT chondrocytes and HDF fibroblasts. Cells were stimulated with Cytomimetic formulations as described in Example 16.

| Sample | HaCaT | | | HDF | | |
|---|---|---|---|---|---|---|
| | \% of wound surface repaired | | | | | |
| | 50 | 80 | 100 | 50 | 80 | 100 |
| | Repair time (h) | | | | | |
| Control | 22 | 33 | 50 | 22 | 36 | 58 |
| Cytomimetic formulation 1% v/v* | 10 | 16 | 20 | 13 | 17 | 21 |
| Cytomimetic formulation 2% v/v* | 7 | 10 | 14 | 8 | 12 | 15 |

*% respect to growth medium

TABLE 14

Antioxidant in vitro activity of Cytomimetic formulation using T-BARS (thiobarbituric acid reactive substances) assay.

| Sample (w/v in DMEM) | Protection during stress treatment* | Protection after stress treatment° | HaCaT | HDF |
|---|---|---|---|---|
| | | | Lipid peroxidation % respect the control | |
| Control | | | 100 | 100 |
| No Cytomimetic | | | 450 | 460 |
| Cytomimetic formulation 0.1% | UV-A | | 130 | 134 |
| Cytomimetic formulation 0.5% | UV-A | | 98 | 100 |
| No Cytomimetic | | | 540 | 530 |
| Cytomimetic formulation 0.1% | $H_2O_2$ | | 120 | 115 |
| Cytomimetic formulation 0.5% | $H_2O_2$ | | 95 | 100 |
| Cytomimetic formulation 0.1% | | UV-A | 128 | 132 |
| Cytomimetic formulation 0.5% | | UV-A | 96 | 100 |
| Cytomimetic formulation 0.1% | | $H_2O_2$ | 133 | 135 |
| Cytomimetic formulation 0.5% | | $H_2O_2$ | 95 | 98 |

*Effect on lipid peroxidation of of 0.1 and 0.5% v/v Cytomimetic formulation present during stress conditions.
**Effect on lipid peroxidation of of 0.1 and 0.5% v/v Cytomimetic formulation v/v applied after stress conditions.

TABLE 15

Effect of Cytomimetic formulation on HSP 70 and HSP 90 induction.

| Sample | Concentration Cytomimetic formulation (% v/v) in the growth medium | | | | |
|---|---|---|---|---|---|
| | 0.0 | 0.1 | 0.2 | 0.5 | 1.0 |
| | HSP 70 expression (respect to the control = 100) | | | | |
| Cytomimetic formulation | 100 | 105 | 130 | 138 | 180 |
| | HSP 90 expression (respect to the control = 100) | | | | |
| Cytomimetic formulation | 100 | 100 | 135 | 141 | 200 |

TABLE 16

Gene expression induced by Cytomimetic formulation.

| Cellular model | HaCaT | | HDF | |
|---|---|---|---|---|
| | Normalized fold expression | | | |
| Cytomimetic concentration (% v/v) | 0.1 | 0.5 | 0.1 | 0.5 |
| CD44 | 6.4 | 8.3 | 6.5 | 7.3 |
| RHAMM | 4.9 | 6.3 | 5.1 | 7.9 |
| TLR-4 | 0.3 | 0.2 | 0.4 | 0.2 |
| TGF-β1 | 6.6 | 8.4 | 6.7 | 9.6 |
| TNFα | 4.1 | 6.7 | 3.9 | 6.4 |
| IL-6 | 1.9 | 2.8 | 2.2 | 4.5 |

TABLE 17

Example of Base formula

| Phase A | Ingredient | Percentage |
|---|---|---|
| A | Water | 60-90% |
| A1 | Glycerin | 3-10% |
| A2 | Glyceryl Polyacrylate | 1-15% |
| A3 | Acrylates Copolymer | 5% |
| A4 | Butylene Glycol | 1-5% |
| A5 | Carbomer | 0.1-1% |
| A6 | Xanthan Gum | 0.1-1% |

| Phase B | OIL PHASE INGREDIENTS | Percentage |
|---|---|---|
| B1 | *Olea Europaea* Fruit Oil | 1-10% |
| B2 | Stearoxymethicone/Dimethicone Copolymer | 0.1-10% |
| B3 | Polymethylsilsesquioxane | 0.1-10% |
| B4 | Polyacrylate-13 | 0.1-10% |
| B5 | HDI/Trimethylol Hexyllactone Crosspolymer | 0.1-10% |
| B6 | Polyisobutene | 0.1-10% |
| B7 | Cholesteryl Nonanoate | 0.1-10% |
| B8 | Hydrogenated Lecithin | 0.1-10% |
| B9 | Polysorbate 20 | 0.1-10% |
| B10 | Cholesteryl Chloride | 0.1-10% |
| B11 | Sodium Acrylates Copolymer | 0.1-10% |
| B12 | Cholesteryl Oleyl Carbonate | 0.1-10% |
| B13 | Silica | 0.1-10% |
| B14 | Methyl Methacrylate Crosspolymer | 0.1-10% |

| Phase C | Preservatives | |
|---|---|---|
| C1 | Phenoxyethanol | 0.1-1.5% |
| C2 | Ethylhexylglycerin | 0.1-3% |
| D | Fragrance | 0.1-10% |

TABLE 18

Example of base formula and of cosmeceutical preparation including Cytomimetic formulations

| Phase A | Ingredient | Percentage |
|---|---|---|
| A | Water | 60-90% |
| A1 | Glycerin | 3-10% |
| A2 | Glyceryl Polyacrylate | 1-15% |
| A3 | Acrylates Copolymer | 5% |
| A4 | Butylene Glycol | 1-5% |
| A5 | Carbomer | 0.1-1% |
| A6 | Xanthan Gum | 0.1-1% |

| Phase B | OIL PHASE INGREDIENTS | Percentage |
|---|---|---|
| B1 | *Olea Europaea* Fruit Oil | 1-10% |
| B2 | Stearoxymethicone/Dimethicone Copolymer | 0.1-10% |
| B3 | Polymethylsilsesquioxane | 0.1-10% |
| B4 | Polyacrylate-13 | 0.1-10% |
| B5 | HDI/Trimethylol Hexyllactone Crosspolymer | 0.1-10% |
| B6 | Polyisobutene | 0.1-10% |
| B7 | Cholesteryl Nonanoate | 0.1-10% |

TABLE 18-continued

Example of base formula and of cosmeceutical preparation including Cytomimetic formulations

| | | |
|---|---|---|
| B8 | Hydrogenated Lecithin | 0.1-10% |
| B9 | Polysorbate 20 | 0.1-10% |
| B10 | Cholesteryl Chloride | 0.1-10% |
| B11 | Sodium Acrylates Copolymer | 0.1-10% |
| B12 | Cholesteryl Oleyl Carbonate | 0.1-10% |
| B13 | Silica | 0.1-10% |
| B14 | Methyl Methacrylate Crosspolymer | 0.1-10% |
| Phase C | Cytomimetic formula | 0.1-10% |
| Phase D | Preservatives | |
| D1 | Phenoxy ethanol | 0.1-1.5% |
| D2 | Ethylhexylglycerin | 0.1-1.5% |
| Phase E | Fragrance | 0.1-10% |

TABLE 19

Clinical results.

| Methodology | Parameter | Initial (average) | Base Cream | Base cream and Cyto | Improvement (%) relative to base formula |
|---|---|---|---|---|---|
| Profilometry | Scaliness (Secc) | 0.90 ± 0.13 | 0.71 ± 0.08 | 0.65 ± 0.08 | 116% |
| | Roughness (Ser) | 3.39 ± 0.36 | 3.16 ± 0.35 | 3.09 ± 0.25 | 76.6% |
| | Smoothness (Sesm) | 46.36 ± 2/50 | 43.38 ± 3.20 | 40.09 ± 3.5 | 47.5% |
| | Wrinkless (Sew) | 47.23 ± 6/56 | 44.09 ± 2.96 | 42.63 ± 2.54 | 73.9% |
| Sebumetry | Oily Skin | 258.65 ± 31/35 | 238.67 ± 17.64 | 202.67 ± 23.02 | 35.67% |
| | Dry Skin | 33.50 ± 9.38 | 96.57 ± 15.42 | 118.38 ± 18.05 | 74.30% |
| Cutometry | Gross Elasticity (R2) | 0.58 ± 0.13 | 0.61 ± 0.09 | 0.63 ± 0.11 | 40.00% |
| | Net Elasticity (R5) | 0.42 ± 0.09 | 0.44 ± 0.13 | 0.46 ± 0.07 | 50.00% |
| Corneometry | Hydration | 73.28 ± 7.25 | 74.24 ± 3.59 | 76.25 ± 7.35 | 33.33% |

What is claimed:

1. A patch consisting essentially of a fermented *tuber magnatum*, olive leaf extract, fermented grape must, hyaluronic acid.

* * * * *